US007184822B2

United States Patent
Kasahara et al.

(10) Patent No.: US 7,184,822 B2
(45) Date of Patent: Feb. 27, 2007

(54) ANIMAL HEALTH CARE SYSTEM

(75) Inventors: Yasuhiro Kasahara, Tokyo (JP); Takashi Shiokawa, Tokyo (JP)

(73) Assignee: Tanita Corporation, Tokyo (JP)

( * ) Notice: Subject to any disclaimer, the term of this patent is extended or adjusted under 35 U.S.C. 154(b) by 373 days.

(21) Appl. No.: 10/785,998

(22) Filed: Feb. 26, 2004

(65) Prior Publication Data

US 2004/0167386 A1    Aug. 26, 2004

(30) Foreign Application Priority Data

Feb. 26, 2003 (JP) ............................. 2003-050007
Jun. 11, 2003 (JP) ............................. 2003-166785

(51) Int. Cl.
A61B 5/05 (2006.01)
(52) U.S. Cl. ...................................... 600/547; 600/506
(58) Field of Classification Search ................ 600/506, 600/547, 554
See application file for complete search history.

(56) References Cited

U.S. PATENT DOCUMENTS

| 1,404,173 | A | * | 1/1922 | Barnard ...................... 119/722 |
| 3,330,258 | A | * | 7/1967 | Rosenberg .................. 119/756 |
| 3,989,036 | A | | 11/1976 | Sasamori |
| 4,170,961 | A | * | 10/1979 | Rosenberg et al. ......... 119/756 |
| 5,133,421 | A | | 7/1992 | Wang |
| 5,335,667 | A | | 8/1994 | Cha et al. |
| 5,372,141 | A | * | 12/1994 | Gallup et al. ............... 600/547 |
| 5,720,296 | A | * | 2/1998 | Cha ............................ 600/554 |
| 5,810,742 | A | * | 9/1998 | Pearlman .................... 600/547 |
| 5,823,957 | A | | 10/1998 | Faupel et al. |
| 6,067,468 | A | | 5/2000 | Korenman et al. |
| 6,208,890 | B1 | | 3/2001 | Sarrazin et al. |

(Continued)

FOREIGN PATENT DOCUMENTS

JP          6-176          1/1994

(Continued)

OTHER PUBLICATIONS

C.A. Stanton et al., "Bioelectrical impedance and zoometry for body composition analysis in domestic cats", Am J Vet Res, vol. 53, No. 2, Feb. 1992, pp. 251-257.

(Continued)

Primary Examiner—Max Hindenburg
Assistant Examiner—Rene Towa
(74) Attorney, Agent, or Firm—McDermott Will & Emery LLP

(57) ABSTRACT

Disclosed is an animal health care system, comprising: a weight input unit; an impedance measurement unit; an inter-leg distance input unit; and a health assessment data calculation unit. According to the present invention said weight input unit enters weight value of an animal, and said impedance measurement unit includes impedance measurement electrodes each for contacting with a root of each leg of the animal and measures impedance between front and rear legs of the animal. Furthermore, said inter-leg distance input unit enters the distance between the roots of front and rear legs of the animal, and said health assessment data calculation unit calculates health assessment data, based on the weight value of the animal, the impedance between front and rear legs of the animal, and the distance between the roots of front and rear legs of the animal.

34 Claims, 17 Drawing Sheets

U.S. PATENT DOCUMENTS

| | | | |
|---|---|---|---|
| 6,265,978 B1 | 7/2001 | Atlas | |
| 6,292,690 B1 * | 9/2001 | Petrucelli et al. | 600/547 |
| 6,472,617 B1 * | 10/2002 | Montagnino | 177/126 |
| 6,478,736 B1 * | 11/2002 | Mault | 600/300 |
| 6,539,310 B2 * | 3/2003 | Shimomura | 702/19 |
| 6,571,200 B1 * | 5/2003 | Mault | 702/182 |
| 6,643,542 B1 * | 11/2003 | Kawanishi | 600/547 |
| 6,850,798 B2 * | 2/2005 | Morgan et al. | 600/547 |
| 6,865,410 B2 * | 3/2005 | Kavet et al. | 600/407 |
| 6,969,350 B1 * | 11/2005 | Hawthorne et al. | 600/300 |

FOREIGN PATENT DOCUMENTS

| | | |
|---|---|---|
| JP | 2003-14405 A | 5/2003 |
| WO | WO 00/28897 | 5/2000 |

OTHER PUBLICATIONS

H. Yoshikawa et al., "Nutritional Physiology and Biochemistry", Feb. 25, 1987, p. 16.

P.B. Pendergrass et al., "A rapid method for determining normal weights of medium-to-large mongrel dogs", BSAVA, 1983, pp. 269-276.

M.C. Scheltinga et al., "Impedance electrodes positioned on proximal portions of limbs quantify fluid compartments in dogs", USA, The American Physiological Society, 1991, pp. 2039-2044.

T. Oshima et al., "Examination of Bio-Impedance Method for Dog's Body Fat Rate Measurement Method", Veterinary Clinical Pathology Academy.

M. Aoyagi, "Healthy Diet for Dog", K.K. Enter Brain, Oct. 27, 2001, pp. 14-15.

* cited by examiner

| "BCS" | RANGE OF BODY FAT RATE(%FAT) |
|---|---|
| 1 | NOT GREATER THAN 5 |
| 2 | $6 \leq \%FAT \leq 14$ |
| 3 | $15 \leq \%FAT \leq 24$ |
| 4 | $25 \leq \%FAT \leq 34$ |
| 5 | NOT LESS THAN 35 |

CYLINDRICAL MODEL

DISTANCE BETWEEN FRONT AND REAR LEGS "L"

TRUNCATED CONE MODEL

DISTANCE BETWEEN FRONT AND REAR LEGS "L"

GIRTH OF WAIST "e"

GIRTH OF CHEST "d"

FIG. 20

ENTER LIVING BODY INFORMATION

WEIGHT VALUE (kg)

BODY FAT RATE (%)

FIG. 21

SELECT KIND OF DOG

YORKSHIRE TERRIER

JAPANESE MIDGET (SHIBA)

BEAGLE

WELSH CORGI

| KIND OF DOG | BODY TEMPERATURE CORRECTION FACTOR |
|---|---|
| CHIHUAHUA | 1.0 |
| YORKSHIRE TERRIER | 1.1 |
| JAPANESE MIDGET (SHIBA), FEMALE | 2.8 |
| JAPANESE MIDGET (SHIBA), MALE | 3.3 |
| BEAGLE | 3.3 |
| ⋮ | ⋮ |
| GOLDEN RETRIEVER, FEMALE | 9.6 |
| GOLDEN RETRIEVER, MALE | 11.3 |
| SAINT BERNARD, FEMALE | 24.1 |
| SAINT BERNARD, MALE | 27.8 |

| ORDINARY ACTION | ACTION LEVEL INDEX |
|---|---|
| REST CONDITION | 1 |
| WALKING | 2.5 |
| LIGHT EXERCISE | 4.0 |
| HARD EXERCISE | 6.2 |

FIG. 26

| WEIGHT VALUE (kg) | BODY TEMPERATURE CORRECTION FACTOR |
|---|---|
| W<5 | 6.0 |
| 5≦W<10 | 5.5 |
| 10≦W<15 | 5.0 |
| ⋮ | ⋮ |
| 55≦W<60 | 0.5 |
| 60≦W | 0 |

ANIMAL HEALTH CARE SYSTEM

BACKGROUND OF THE INVENTION

1. Field of the Invention

The present invention relates to an animal health care system for effecting health care for various kinds and sizes of animals by measuring weight and impedance of the animals and calculating health assessment data such as body fat rate, body water mass and the like for assessing health condition of the animals.

2. Prior Art

In the conventional health care for animals, in order to judge the degree of adiposity of a dog and a cat, for example, it was common for a veterinary to perform an ocular inspection or a palpation for judging the degree of adiposity using Body Condition Score (hereafter referred to as "BCS") which classifies the animal into five ranks from slender to fat (see non-patent document 1, for example).

A number of researches have previously been conducted in which bioelectrical impedance of an animal is measured and the data such as body fat rate, body water mass and the like is calculated, as in the case of human being. Various kinds of animals such as a dog, a cat, a sheep, a pig, a rat, etc., have been used in those researches as the specimen. Several types of method for impedance measurement and for electrode placement have been developed, but most of them are of invasive type, that is to say, a needle-like electrode is pierced into the skin of the animal for impedance measurement. Then, any correlation between the resultant impedance value and the body composition analysis due to "DEXA" measurement or the dead body analysis is examined. Among others, the following two researches have been disclosed wherein the specimen is a dog and the impedance measurement is conducted in non-invasively without any injury to the animal.

In a first research, a dog is suspended by a fixing device in such manner that the dog is restricted in posture while standing on all four legs, but spaced away from the floor. A measurement person wears a set of gloves on both hands each having a current supplying electrode for impedance measurement affixed on the palm portion thereof, and grasps both front legs of the dog at the predetermined positions for making contact the electrodes on the gloves therewith. Then, another person wearing a set of gloves having voltage measurement electrodes affixed thereto grasps both rear legs of the dog in the same manner for conducting measurement of impedance between the front and rear legs of the dog.

According to the well known theorem for impedance measurement in which body water mass is proportional to square of distance between impedance measurement points, but inversely proportional to the impedance value, the body length of the dog is separately measured, which is used instead of the distance between impedance measurement points, the body water mass is estimated based on the body length and the impedance value, and the body fat rate is calculated based on the body water mass thus estimated and the weight value separately measured. (see non-patent document 2, for example)

In a second research, it is assumed that when the impedance measurement is done by positioning the electrodes at the root of legs that are near to the main body with body hair shaved then more stable impedance value is resulted than when the electrodes are positioned on the legs that are far away from the main body. Therefore, while the dog is sleeping with the face upward under anesthesia the impedance measurement is done diagonally across the body between the front right and rear left legs or between the front left and rear right legs. Again, according to the well known theorem for impedance measurement in which body water mass is proportional to square of distance between impedance measurement points, but inversely proportional to the impedance value, the body length of the dog is separately measured, which is used instead of the distance between impedance measurement points, and the body water mass is estimated based on the body length and the impedance value. (see non-patent document 3, for example)

Further research has been disclosed in which the weight value is estimated according to regression formula which is derived based on correlation between the weight value and each morphologic measurement value such as body length, body height or girth of trunk of an animal. Among those, the highest correlation is resulted between the weight value and the girth of trunk, which is illustrated as correlation factor "r"=0.85. (see non-patent document 4)

Furthermore, it is well known that the metabolism of an animal in rest condition or the basal metabolism of an animal depends on its body temperature. In case of a human, calculation of metabolism based on fat free mass is conducted using the body temperature as the correction term (see non-patent document 5, for example).

The reference documents are as follows:

Non-patent document 1: "Healthy Diet for Dog", Masayuki Aoyagi, K. K. Enter Brain, Oct. 27, 2001, pages 14 to 15;

Non-patent document 2: "Examination of Bio-Impedance Method for Dog's Body Fat Rate Measurement Method", Tomoko Oshima, Fumio Nakato, and two others, VETERINARY CLINICAL PATHOLOGY ACADEMY, Non-patent document 3: "Impedance electrodes positioned on proximal portions of limbs quantify fluid compartments in dogs", MARC R. SCHELTINGA, and four others, USA, the American Physiological Society, 1991;

Non-patent document 4: "A rapid method for determining normal weights of medium-to-large mongrel dogs", PAULA B. PENDERGRASS, and four others, BSAVA, 1983; and Non-patent document 5: "Nutritional Physiology and Biochemistry", Harutoshi Yoshikawa, K. K. Koseikan, Feb. 25, 1987, Page 16.

However, judgment for degree of adiposity for an animal using "BCS" is governed by subjectivity of a veterinary who conducts an ocular inspection or a palpation, which highly depends on experience and perception of the veterinary, and therefore, there is tendency that the result of judgment varies widely or there is possibility that misjudgment is made. In addition, in case where an owner of an animal having no professional skill readily conducts judgment of adiposity of the animal at home there may possible that the result of judgment varies more and more widely. As the result, it may happen that the animal is given too much food, thereby making the animal more adipose, or inversely the animal becomes too slender, thereby loading greater burden to the animal.

Although many researches for measurement of impedance of an animal have been made, as described above, most of them are of invasive type so that they are impractical in the relevant field. In addition, two specific researches are described above wherein the specimen is a dog and the impedance measurement is conducted in non-invasively to derive body fat rate, body water mass, etc., as in the case of human being. However, as described above, in the first research, the fixing device is necessary for fixing the dog while it is suspended. In such case, when measurement of bigger dog is necessary, the size of the fixing device should be increased accordingly. Furthermore, in order to make contact the electrodes to both front legs and both rear legs of the dog, two persons are necessary to grasp the legs of the dog, which is very tedious task. In this regard, there is possibility of an error occurred in measurement due to misalignment of the electrode to the predetermined position of the leg depending on the manner the person grasps the leg. Moreover, it is necessary to separately measure the weight and body length of the dog for calculating the health assessment data such as body fat rate, body water mass, etc., which takes longer period of time and needs much labor. The body length separately measured is simply used instead of the distance between the measurement electrodes, which may be an error source for calculation of the health assessment data, for example.

In the second research, because of substantially no such animals that are immobile with the face upwardly during the measurement of impedance, it is necessary that the animal sleeps under anesthesia, which is impractical irrespective of the fact that the impedance measurement can be conducted in non-invasively. Again, the body length of the animal is separately measured and used instead of the distance between the measurement electrodes, which may be an error source for calculation of the health assessment data.

In this manner it can be said that technique for measurement of bio-impedance of an animal still remains in the course of studying and research phase and no systems for readily conducting animal health care and suitable for practical use have been provided.

In addition, the system for estimating weight value using the regression formula derived from the correlation between the weight value and the girth of trunk of an animal has not been studied to such level that the health care of the animal is effected using the estimated weight value.

Furthermore, such living body measurement system has been well known that acts as a human adiposity judgment system for indicating tendency of adiposity for human by measuring body fat rate using "BIA" technique. However, no animal body fat rate calculation system in which various kinds of and different sizes of animals can be accepted for measurement has been put into practice.

Moreover, in case of an animal, especially, a dog, the body temperature depends on its body build and varies widely over various kinds of dogs. The metabolism of dog can be calculated using the fat free mass and the body temperature, as in the case of a human whose metabolism is previously calculated using the body temperature as the correction term. But, measurement of body temperature of dog takes longer period of time because of temperature of rectum mainly measured, which makes the temperature measurement very difficult.

Because of no device developed for calculating consumption and intake energy for each of dogs it has been common that food is given without knowing the proper amount for the dog. Accordingly, there may happen that food is given too much or too less, with the result that insufficient health care including adipose condition can frequently be resulted.

In view of the above, an object of the present invention is to provide an animal health care system that conveniently allows health care of an animal even at home.

Another object of the present invention is to provide a dog health care system for effecting health care for dog by deriving the metabolism of dog that is corrected using body temperature correction factor according to kinds or body builds of dogs.

SUMMARY OF THE INVENTION

In order to attain such object the present invention provides an animal health care system, comprising: a weight input unit; an impedance measurement unit; an inter-leg distance input unit; and a health assessment data calculation unit, wherein said weight input unit enters weight value of an animal, said impedance measurement unit includes impedance measurement electrodes each for contacting with a root of each leg of the animal and measures impedance between front and rear legs of the animal, said inter-leg distance input unit enters the distance between the roots of front and rear legs of the animal, and said health assessment data calculation unit calculates health assessment data based on the weight value of the animal, the impedance between front and rear legs of the animal, and the distance between the roots of front and rear legs of the animal.

The impedance measurement electrode is formed from flexible electrically conductive material including either of electrically conductive resin and electrically conductive rubber, or it comprises an electrically conductive member having a spherical portion or a spring-like portion formed thereon for contacting with the skin of the animal.

The impedance measurement electrode has a plurality of projected portions formed on the surface thereof for making sure to contact with the skin of the animal irrespective of presence of body hear.

The impedance measurement electrode has a cushion material including either of sponge and cloth, provided on the surface thereof for providing water-keeping capability.

The impedance measurement electrode includes a constant pressure unit for producing constant pressure to make contact with the animal at the level of not stimulating the animal.

The health assessment data calculation unit calculates the health assessment data by taking into account of at least one of morphologic measurement data including body length, body height, girth of trunk, girth of chest or girth of waist of the animal.

The weight input unit includes a restriction unit by which at least one of the chest, abdomen, legs and roots of legs of the animal is placed and kept in position, and measures and enters the weight of the animal while restricting it in such manner that no legs of the animal are contact with those other than the restriction unit.

The restriction unit includes contact portions each for contacting with the root of each leg of the animal, and automatically measures and enters the distance between the contact portions, thereby also acting as the inter-leg distance input unit.

The restriction unit includes contact portions each for contacting with the root of each leg of the animal and each provided with the impedance measurement electrode, thereby also acting as the impedance measurement unit.

In another aspect, the present invention provides an animal health care system, comprising: a weight input unit; an estimated weight calculation unit; and a health assessment data calculation unit, wherein said weight input unit enters weight value of an animal, said estimated weight calculation unit calculates an estimated weight value based on at least girth of the trunk of the animal among the morphologic measurement data including at least one of girth of the trunk, body length and body height of the animal, and said health assessment data calculation unit calculates health assessment data based on the difference between the weight value and the estimated weight value.

The weight input unit includes a restriction unit by which at least one of the chest, abdomen, legs and roots of legs of the animal is placed and kept in position, and measures and enters the weight of the animal while restricting it in such manner that no legs of the animal are contact with those other than the restriction unit.

The restriction unit has its width or height for receiving the animal, which can be adjusted according to the size of the animal.

The restriction unit includes a flexible net or meshed sheet through which at least four legs of the animal can pass, and frames for securing the net at any condition from spread condition to folded condition.

The restriction unit further includes a lift unit on which said frame is secured, and as the height of the lift unit is increased the spacing between two said frames becomes narrower.

The health assessment data calculated by the health assessment data calculation unit is body water mass of the animal.

The health assessment data calculated by the health assessment data calculation unit is fat free mass of the animal.

The health assessment data calculated by the health assessment data calculation unit is body fat mass of the animal.

The health assessment data calculation unit includes a "BCS" (Body Condition Score) estimation unit for estimating "BCS" based on the health assessment data calculated.

The health assessment data calculation unit includes an adiposity judgment unit for judging the degree of adiposity of the animal based on the health assessment data calculated.

In further aspect the present invention provides an animal health care system, comprising: a fat free data input unit; a body temperature related data input unit; a body temperature correction factor derivation unit; and a metabolism calculation unit, wherein said fat free data input unit enters fat free data of a dog,
said body temperature related data input unit enters body temperature related data of the dog,
said body temperature correction factor derivation unit derives body temperature correction factor based on said body temperature related data, and
said metabolism calculation unit calculates metabolism of the dog based on said fat free data and said body temperature correction factor.

The fat free data is fat free mass or amount of muscle.

The fat free data is derived from weight value and body fat data.

The body temperature related data is kind of dog.

The body temperature related data is body build of the dog.

The body build of the dog is body mass index estimated from the weight value.

The metabolism calculation unit includes a body hair data input unit for entering body hair data of the dog, and calculates the metabolism of the dog by taking into account of the body hair data entered thereby.

The metabolism calculation unit includes an age input unit for entering the age of the dog, and calculates the metabolism of the dog by taking into account of the age.

The metabolism calculation unit includes a thermal insulation effect factor derivation unit for deriving thermal insulation effect factor based on the body fat rate of the dog when it is entered thereto, and calculates the metabolism of the dog by taking into account of said thermal insulation effect factor.

The metabolism calculation unit calculates at least one of the basal metabolism and the metabolism in rest condition.

The metabolism calculation unit includes an action data input unit for entering action data of the dog and a total energy consumption calculation unit for calculating total energy consumption of the dog based on the metabolism and the action data.

The action data is action factor indicating ordinary action of the dog with a plurality of steps.

The action data is exercise data measured by an exercise monitoring device including at least one of a pedometer and an accelerator.

The total energy consumption calculation unit includes an adiposity related data input unit for entering adiposity related data of the dog, a target weight reduction setting unit for setting target weight reduction, and a proper value calculation unit for calculating at least one of proper intake energy or proper consumption energy relative to said target weight reduction, based on said total energy consumption, said adiposity related data and said target weight reduction.

The adiposity related data is weight value and body fat data of the dog.

The body fat data is body fat mass or body fat rate calculated using at least one of impedance value of the dog, body condition score or morphologic measurement data.

The target weight reduction is a general standard value for adiposity that is automatically set as the target.

The target weight reduction is set by a measurement person who manually enters numerical value.

The total energy consumption calculation unit includes an ambient temperature input unit for entering ambient temperature, and calculates total energy consumption by taking into account of the ambient temperature.

The ambient temperature is set in advance for every season or every month so that it is automatically entered.

BRIEF DESCRIPTION OF THE DRAWINGS

The present invention will now be described in more detail with reference to the accompanying drawings, in which:

FIG. 20 is a view illustrating one example of display screen;

FIG. 21 is a view illustrating another example of display screen;

FIG. 26 is a table listing body temperature correction factors and the corresponding weight values of dogs.

DESCRIPTION OF THE PREFERRED EMBODIMENTS

The present invention will now be described in more detail with reference to a first embodiment of an animal health care system in which while an animal is restricted in posture the weight value, impedance value and distance between front and rear legs of the animal are automatically measured and the body fat rate of the animal is calculated as health assessment data, thereby allowing judgment of the degree of adiposity of the animal.

Figure 1:
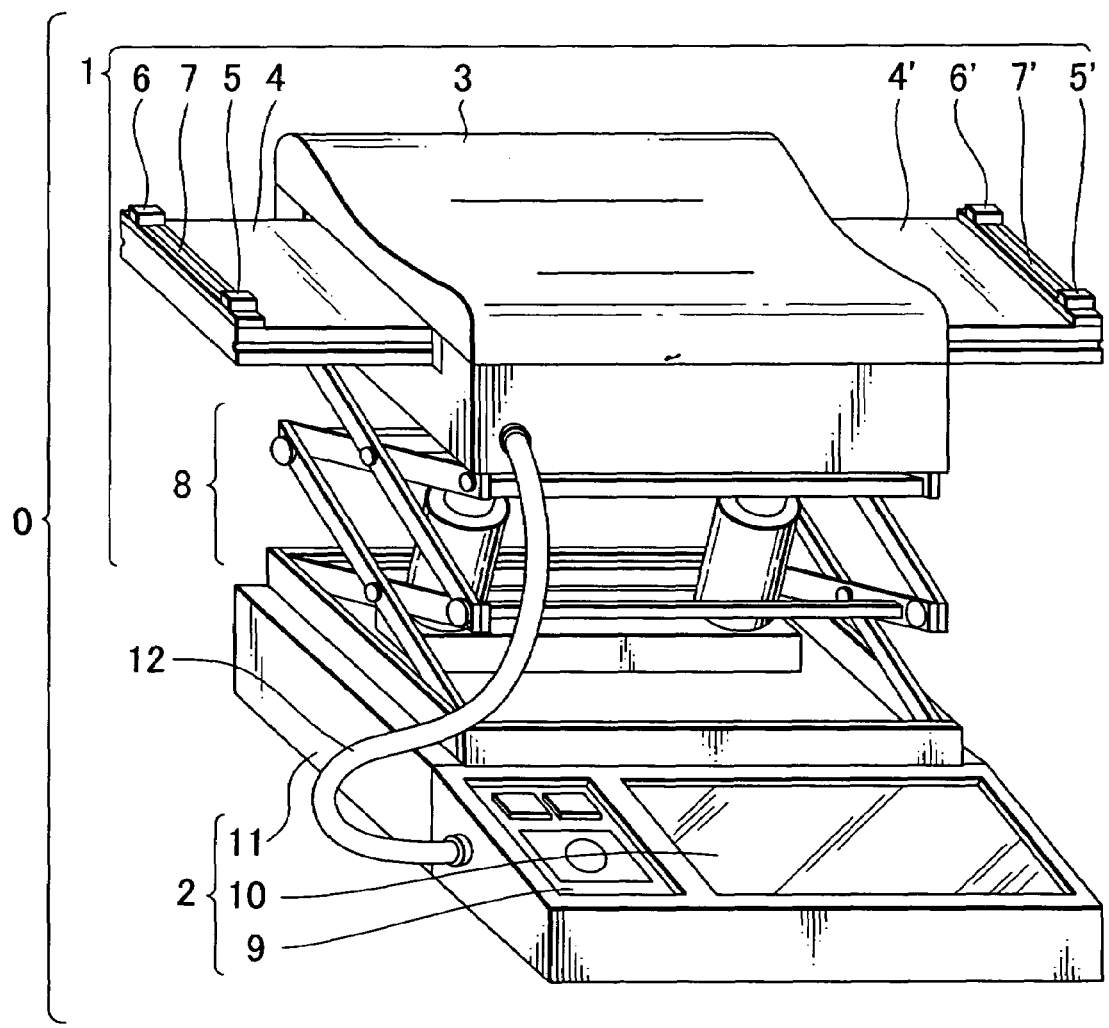
FIG. 1 is an external view of an animal health care system according to a first embodiment of the present invention.
Figure 2:
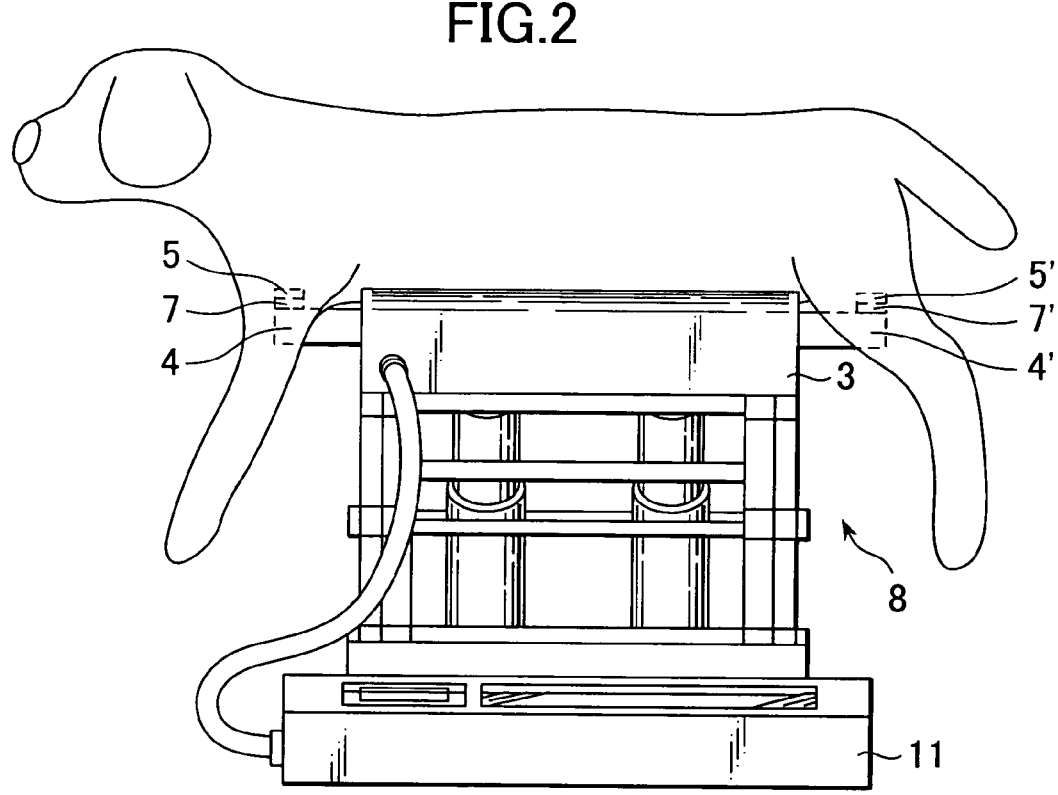
FIG. 2 is a front view of the animal health care system when it is actually used.
Figure 3:
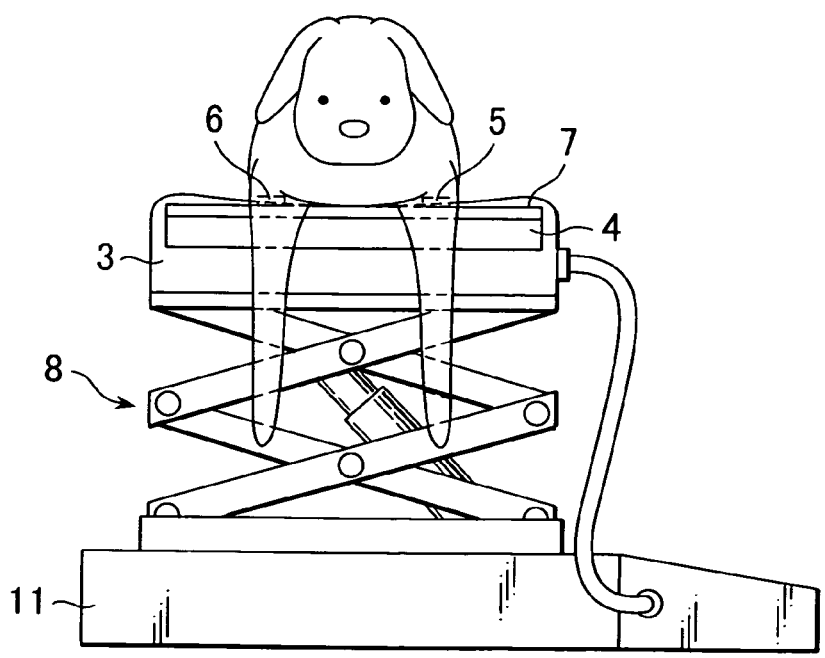
FIG. 3 is a side view of the animal health care system when it is actually used.
Figure 4:
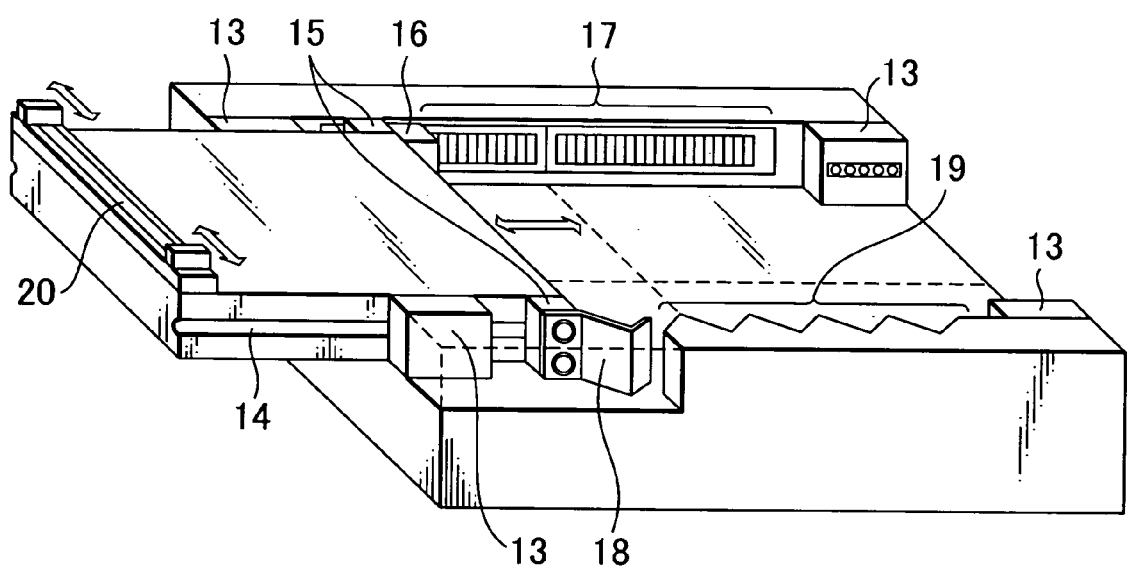
FIG. 4 is a perspective view partially illustrating inside of the animal health care system.
Figure 5:
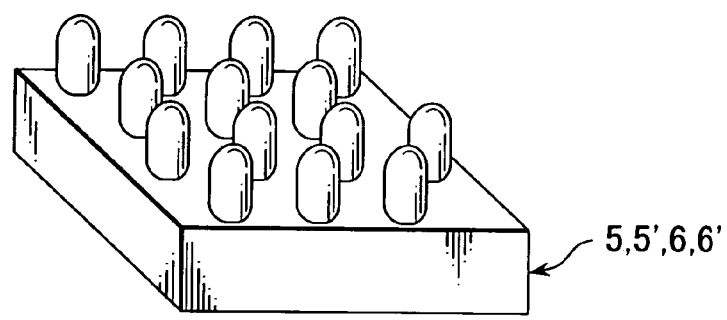
FIG. 5 is an enlarged view of an electrode surface.
Figure 6:
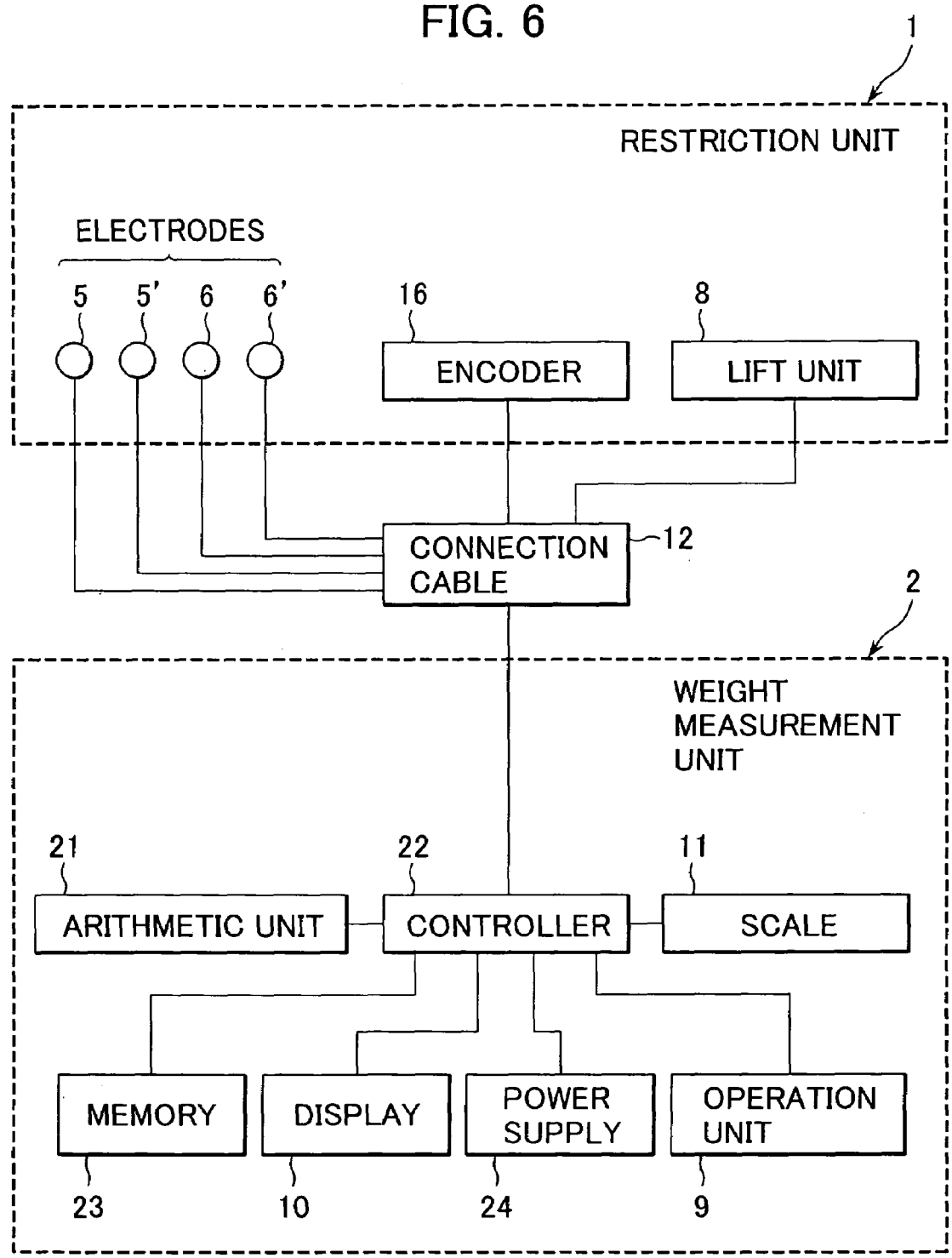
FIG. 6 is a functional block view of the first embodiment.

The first embodiment of the present invention will be described in conjunction with FIGS. 1 to 6. In particular, FIG. 1 is an external view of the animal health care system according to the first embodiment; FIG. 2 is a front view of the animal health care system when it is actually used; FIG. 3 is a side view of the animal health care system when it is actually used; FIG. 4 is a perspective view partially illustrating the inside of the animal health care system; FIG. 5 is an enlarged view of an electrode surface; and FIG. 6 is a functional block view of the first embodiment.

Referring now to the external view of FIG. 1, the animal health care system 0 comprises a restriction unit 1 by which an animal is restricted in such posture that it is standing on all four legs and a weight measurement unit 2 for measuring the weight of the animal while it is restricted by the restriction unit 1. The restriction unit 1 includes a platform 3 on which a chest and abdomen region of the animal is placed, a front leg auxiliary support 4 and a rear leg auxiliary support 4' which can be drawn to and held at the positions where they become contact to the roots of front and rear legs of the animal from the platform 3 according to the distance between the front and rear legs of the animal, and a lift unit 8 for changing the height between the weight measurement unit 2 and the platform 3 in order to make the four limbs of the animal floated, spaced away from the weight measurement unit 2.

Referring to FIGS. 2 and 3, the front leg auxiliary support 4 is provided with, at one end portion thereof, a current supplying electrodes 5 and a voltage measurement electrode 6 each for contacting to the root of each of front right and left legs of the animal for impedance measurement, and an electrode slider 7 on which the electrodes 5 and 6 are slidably mounted. In the same manner, the rear leg auxiliary support 4' is provided with a current supplying electrodes 5' and a voltage measurement electrode 6' each for contacting to the root of each of rear right and left legs of the animal for impedance measurement, and an electrode slider 7' on which the electrodes 5' and 6' are slidably mounted. Accordingly, the measurement of impedance is performed according to "four-electrode method" in which a weak current is fed through between the front and rear legs and a potential across the front and rear legs is measured.

Referring to FIG. 4, a motion mechanism for the front leg auxiliary support 4 and the rear leg auxiliary support 4' will be described in more detail.

The front and rear leg auxiliary supports 4 and 4' can horizontally be drawn from the platform 3 and they include a well known ball slider mechanism. In particular, each of the auxiliary supports 4 and 4' is provided with ball linear guides 13 at both sides thereof each having a plurality of hard balls linearly arranged thereon. In order to engage with the balls in the ball linear guide 13 a guide channel 14 is formed on each auxiliary support at each of both sides thereof. The balls in the ball linear guide 13 can roll within the guide channel 14 so that the auxiliary support can smoothly be moved. In this embodiment each of the auxiliary support 4 and 4' can manually be drawn.

In addition, at another end portion of each auxiliary support 4, 4' that is opposite to the end portion wherein the electrode slider 7, 7' is mounted, a stopper 15 is mounted to each auxiliary support 4, 4' at each of both sides thereof for preventing each auxiliary support from coming off when it is drawn from the platform 3. One of the stoppers 15 for each auxiliary support is provided with a prior art encoder 16. Correspondingly, an encoder guide 17 is mounted on an internal side surface of the platform 3 for the purpose of reading the distance by the encoder 16. Then, the distance over which each auxiliary support 4, 4' is drawn is automatically measured. Each auxiliary support 4, 4' is to be drawn up to the position at which it becomes contact to the root of each of front and rear legs of the animal. Therefore, the distance over which each auxiliary support 4, 4' is drawn is used to easily derive the distance between front and rear legs of the animal.

The other stopper 15 is provided with an angled leaf spring 18 which is engaged with a corrugated positioning guide 19 mounted on an opposite internal side surface of the platform 3. Therefore, it is possible to hold each auxiliary support 4, 4' at such position that it is drawn.

Although not shown, each of the electrodes 5, 5', 6, 6' and each of the electrode sliders 7, 7' are moved using the same prior art ball slider mechanism as that described above. In particular, the electrodes 5, 5', 6, 6' are manually slid.

Referring to FIG. 5, the surface of each of the electrodes 5, 5', 6, 6' is illustrated in enlarged view. A plurality of projections each having a spherical end portion formed thereon are provided on the electrode surface to thrust through the body hair to surely contact to the skin of the animal.

The lift unit 8 may be formed from so called "height variable" mechanism such as well known jack and lift. In this embodiment an electrically powered lift that is operated via a separate operation unit is provided as the lift unit 8.

The weight measurement unit 2 includes a scale 11 for measuring the weight of the animal, an operation unit 9 including a power switch and other elements for operation of the system, a display unit 10 for displaying the weight value, impedance value, measured values such as distance between front and rear legs, and result of judgment for adiposity of the animal.

The restriction unit 1 and the weight measurement unit 2 are connected to each other via a connection cable 12 for signal communication therebetween.

The procedure for restriction of an animal in the animal health care system 0 will be described hereafter. At first, the animal is carried on the system with a chest and abdomen region thereof placed on the platform 3, and then, the front and rear leg auxiliary supports 4 and 4' received in the platform 3 are drawn according to the body length of the animal until the roots of front and rear legs thereof are placed on the front and rear leg auxiliary supports 4 and 4', respectively. The front and rear leg auxiliary supports 4 and 4' are held at such position that they are drawn with the aid of the angled leaf spring 18 and the positioning guide 19. At the same time, the distance over which the front and rear leg auxiliary supports 4 and 4' are drawn is automatically measured by the encoder 16 and the encoder guide 17.

Then, the electrodes 5, 5', 6, 6' slidably mounted on the electrode sliders 7, 7' are manually slid until they become contact to the roots of four limbs of the animal. Therefore, it is possible to measure the impedance between the roots of front and rear legs of the animal.

Due to the fact that the animal is placed on the system with the roots of four limbs thereof supported on the front and rear leg auxiliary supports 4 and 4' so that an extent of each leg from its root to its tiptoe is completely floated without any portion contact to the health care system 0 it is possible to measure the weight of the animal by the weight measurement unit 2 while the animal is restricted by the restriction unit 1 in such manner that the height of the lift unit 8 is adjusted via the operation unit 9 to float the animal. In addition, because the animal is placed on the system with the roots of four limbs thereof supported, as described above, the limbs of the animal become free and the animal can apply no power to the limbs. As the result, the movement of the limbs can be limited, thereby preventing the animal from suddenly running or acting violently.

According to the configuration, as described above, when setting the electrodes 5, 5', 6, 6' the distance over which the front and rear leg auxiliary supports 4 and 4' are drawn is automatically measured, and therefore, by taking account of the original length of the platform 3, the distance between the front and rear legs of the animal, i.e., the distance between the impedance measurement electrodes can easily be determined. Accordingly, unlike the prior art system in which the body length of the animal is used instead of the distance between impedance measurement electrodes, it becomes possible to produce highly precise health assessment data.

Furthermore, the animals that can be measured by the present system are those having four limbs and allowing operation of supplying the current through the body and measuring the voltage across the body, except for such animals that have hardened skin around the roots of limbs such as a crocodile, a rhinoceros, etc. For example, any kind of dogs can be measured, irrespective of its types such as big type, small type, long hair type, short hair type, etc.

Referring to the functional block diagram of FIG. 6, the functional configuration of the animal health care system will be described. In the animal health care system 0 the restriction unit 1 is connected to the weight measurement unit 2 via the connection cable 12. In particular, the current supplying electrodes 5, 5' and the voltage measurement electrodes 6, 6' as well as the encoder 16 for measuring the distance over which the front and rear leg auxiliary supports 4 and 4' are drawn, all within the restriction unit 1, are connected to a controller 22 within the weight measurement unit 2 via the connection cable 12. The lift unit 8 for changing the height of the platform 3 relative to the weight measurement unit 2 is also connected to the controller 22.

In the weight measurement unit 2 a scale 11 for measuring the weight is connected to the controller 22 which is, then, connected to an arithmetic unit 21 for calculating the body fat rate from measurement data and for judging the adiposity. Furthermore, the controller 22 is connected to a memory 23 for storing measurement result and criterion for judgment of adiposity, a display unit 10 for displaying measurement data and result of judgment of adiposity, a power supply 24 for supplying power to the animal health care system 0, and an operation unit 9 for power supply switching and measurement operation.

Figure 7:
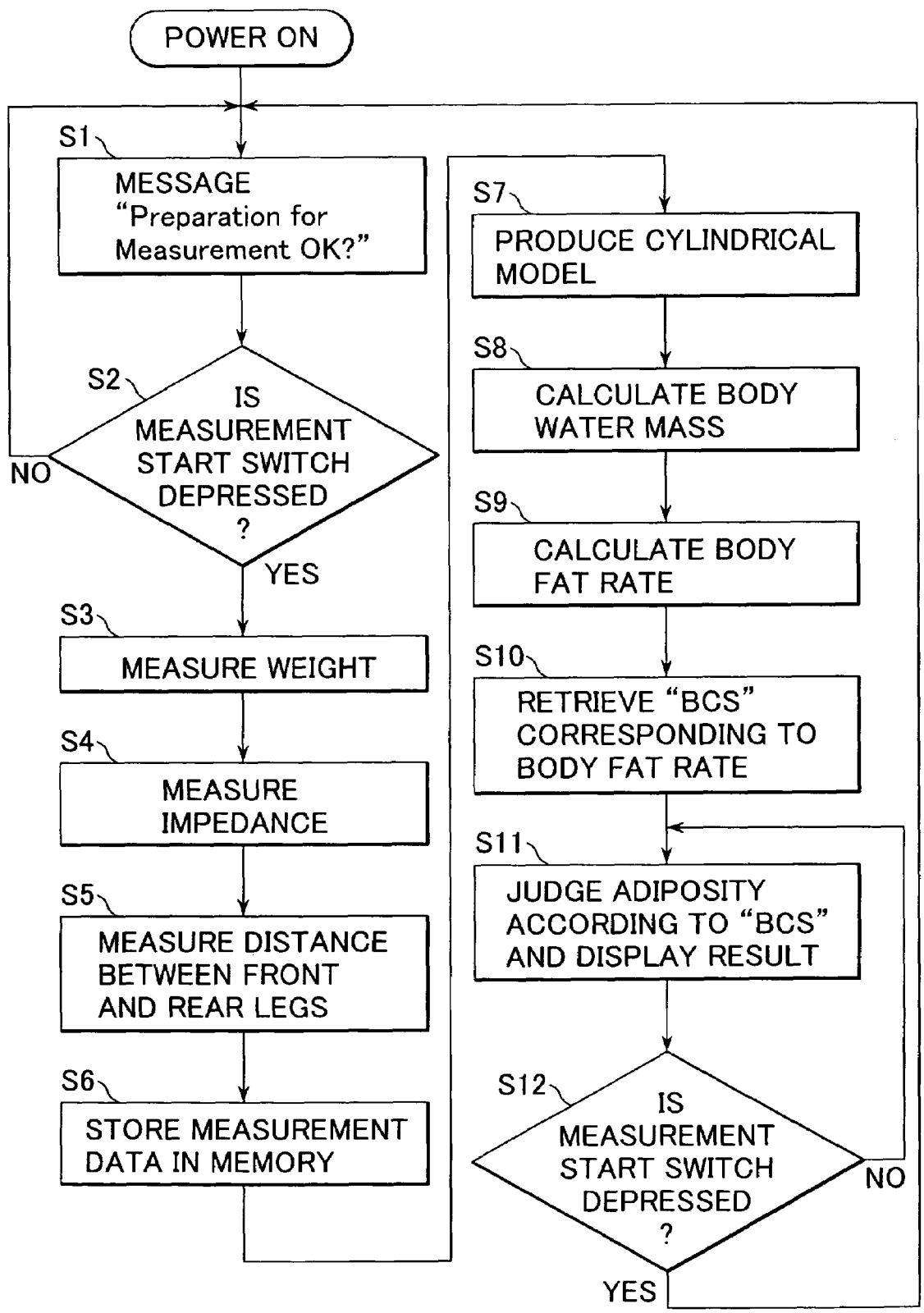
FIG. 7 is a flow chart illustrating an operation of the animal health care system.
Figures 8, 9, 10:
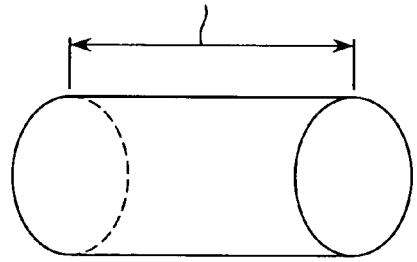
FIG. 8 is a list showing relation between body fat rate and "BCS"
FIG. 9 is a view illustrating one example of morphologic model for an animal.
FIG. 10 is a view illustrating another example of morphologic model for an animal.

One example of process for judging the adiposity of a dog as the specimen according to the animal health care system 0 configured as described above will be described in more detail with reference to FIGS. 7 to 9. In particular, FIG. 7 is a flow chart illustrating an operation of the animal health care system; FIG. 8 is a list showing relation between body fat rate and "BCS"; FIGS. 9 and 10 each illustrates morphologic model for an animal.

Referring to FIG. 7, at first, the power switch on the operation unit 9 is depressed to turn ON the power supply for the animal health care system 0. Then, at step S1 in FIG. 3, a message is displayed for prompting to perform for measurement by restricting a dog in the restriction unit 1 as the specimen, and to push the measurement start switch on the operation unit 9 after the preparation for measurement has been done. Next, at step S2, a check is made to determine whether the measurement start switch on the operation unit 9 is depressed or not. If the answer is NO, the routine proceeds back to step S1 to once again display the message.

But, if the measurement start switch on the operation unit 9 is depressed and the answer on the decision step S2 is YES then the measurement for the dog is started.

At step S3 the weight value of the dog restricted in the restriction unit 1 is measured. Then, at step S4 the impedance between the roots of front and rear legs of the dog is measured. Next, at step S5 the distance between the front and rear legs of the dog is calculated based on the distance of movement of front and rear leg auxiliary supports measured by the encoder 16 and the length of the platform 3. Thereafter, at step S6 the weight value, the impedance value and the distance between front and rear legs are stored in memory 23.

Then, at step S7 a morphologic model for the dog is produced according to the distance between front and rear legs that has been calculated. It is noted, here, that a cylindrical model having the distance "L" between front and rear legs is produced. Based on this cylindrical model, at step S8, the body water mass of the dog is calculated according to the body water mass calculation formula that is well known in the art, as in the case of the human being.

More specifically, the body water mass "V" is calculated according to the following formula:

$$V = L^2/(\sigma \times Z)$$

Where "V"=body fat mass (kg), Z=impedance, and σ=electrical conductivity of water.

At step S9 the body fat rate of the dog is estimated based on this body water mass "V" according to a common calculation formula, as in the case of the human being. In particular, it is assumed that the weight value as measured in step S3 is represented by "W" (kg); the fat free mass is represented by "X" (kg); and the body fat mass is represented by "F" (kg). It is commonly known that in case of human being the rate of the body water mass occupied in the fat free mass "X" (kg) is approx. 73.2 (%) and this is generally applies to the case of animals. Then, the fat free mass "X" (kg)=V/0.732. In addition, the body fat mass "F" is calculated by the formula: "F" (kg)=weight value "W" (kg)−fat free mass "X" (kg). Accordingly, the body fat rate (% FAT) is calculated by the formula: "% FAT"=(F/W)×100.

Then, at step S10, "BCS" that is the conventional criterion for dog adiposity judgment is estimated using the calculated body fat rate as the objective index. In particular, the data of relation between the body fat rate and "BCS", as shown in FIG. 8, is read from the memory unit 23. The "BCS" is ranked into five levels each having the preset range of body fat rate, as shown in FIG. 8. Then, at step S11, "BSC" corresponding to the body fat rate calculated at step 9 is selected according to the data of relation between the body fat rate and "BCS", the degree of adiposity is judged and the result of judgment is displayed on the display unit 10.

Next, at step S12, a check is made to determine whether the measurement start switch on the operation unit 9 is depressed or not. If NO, the routine proceeds back to step S11 so that the result of judgment for adiposity of the dog continues to be displayed. But, if the measurement start switch on the operation unit 9 is depressed and the answer of step S12 is YES, then the routine restores to step S1 for preparation of new measurement.

As described earlier with reference to FIG. 3 the impedance measurement electrode 6 has a plurality of projections formed on the surface thereof each having a spherical end portion. The electrode may be formed from any material such as metal, resin or rubber, provided that it is electrically conductive. Furthermore, the electrode may have a spring-like portion to provide resiliency when it is pushed against the skin of the animal even if it has no spherical end portion.

As also described above, when the impedance measurement electrodes are mounted to the animal they are depressed to the roots of four limbs of the animal due to their own body pressure. In addition, because of the cushion material such as sponge, cloth, etc., provided on the surface of the electrode for providing water-keeping capability, the electrode is made contact to the skin of the dog via the water of which electrical conductivity is extremely higher. Therefore, impedance measurement can be done even using an electrode having a flat surface without degrading the precision for measurement.

Although, in the above description, the electrodes 5, 5', 6, 6' are made contact to the roots of four limbs of the dog, respectively, they may be positioned between the front and rear legs at either one of right and left-hand sides thereof. For example, the current supplying electrodes 5, 5' may be positioned on the dog only at the left-hand side thereof and the voltage measurement electrodes 6, 6' may be positioned immediately inwardly adjacent the current supplying electrodes on a straight line that connects them together. According to such arrangement of the electrodes the current path is positioned near the voltage measurement points so that more stable measurement can be done.

As also described above, at step S7 in the flow chart of FIG. 7, the cylindrical model produced only based on the distance "L" between front and rear legs, as shown in FIG. 9, is used as the morphologic model for the animal. It is possible to produce a more accurate morphologic model by additionally taking into account of the girth of main body of the animal. The following three sizes are defined, here, as the girth of main body of the animal: a first size is the girth of chest "d" around the portion of the body including the roots of both front legs; a second size is the girth of waist "e" around the portion of the body including the roots of both rear legs; and a third size is the girth of trunk "C" around the largest sized portion of the main body.

In this embodiment the girth of chest "d" and the girth of waist "e" are measured in advance, which are taken into account in addition to the distance "L" between the front and rear legs to produce a more accurate morphologic model for the animal in the form of truncated cone, as shown in FIG. 10. Because the impedance measurement means measurement of electrical resistance of the body it depends on the length and the thickness of the current flowing path, that is to say, the distance between front and rear legs of the morphologic model and the area between the measurement points. Accordingly, the body water mass calculation formula used in step S8, as described above, may be replaced by the following formula: $V=(L^2 \times d \times e)/(\sigma \times Z)$, which produces the body water mass with more higher precision.

If the while body impedance is estimated from the truncated cone model it is more preferable to add the morphologic measurement data such as body height, leg length, etc., to produce more accurate morphologic model.

In body fat rate calculation process performed in steps S8 and S9 in addition to step S7 the calculation formula for calculating the body fat rate for a human being is used, as described above. Alternatively, the regression formula for calculating the body fat rate for an animal may be provided and stored in the memory 23, which allows calculation of more precise body fat rate for the animal. In the same manner, the regression formulae for body water mass, fat free mass, etc., may be stored in the memory 23 for calculation.

Figure 11:
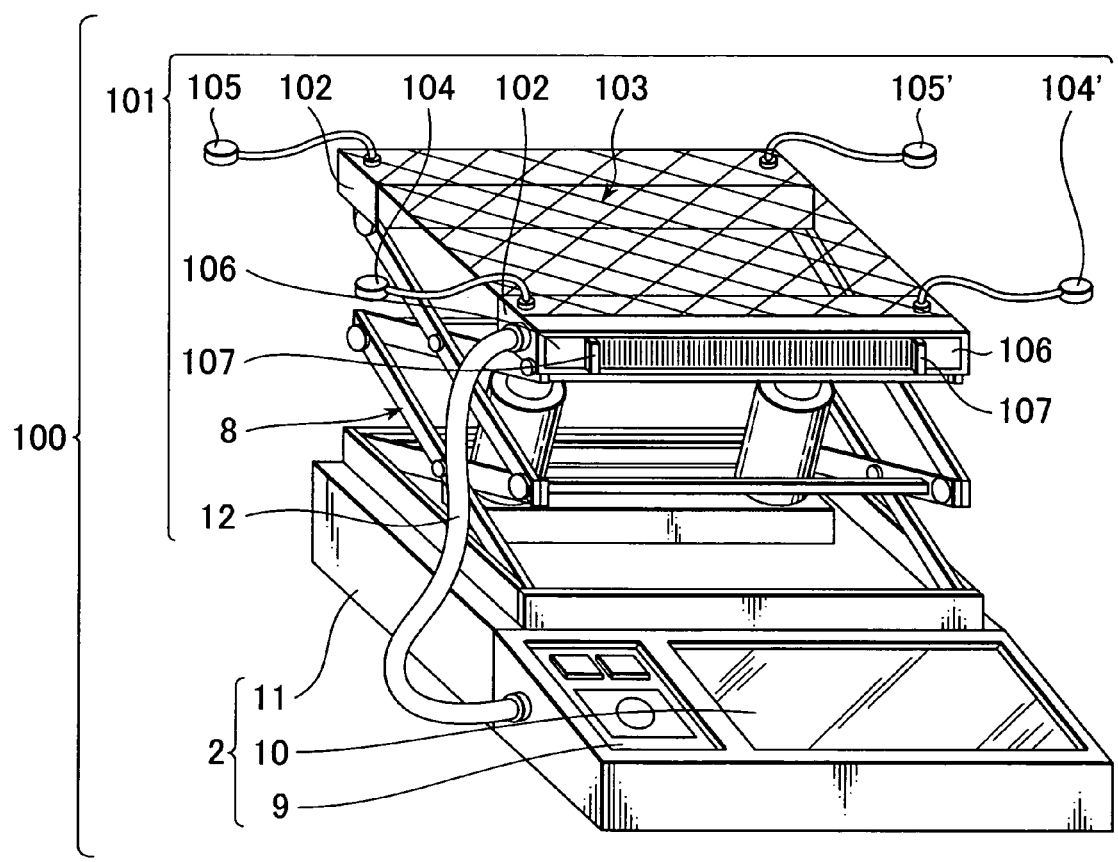
FIG. 11 is an external view of an animal health care system of second embodiment.

Now, a second embodiment of an animal health care system 100 according to the present invention will be described, which is substantially same as the first embodiment, as described above with reference to FIGS. 1 to 4, except that the restriction unit 1 is replaced by another one that is shown in FIG. 11.

More particularly, the animal health care system 100 comprises a restriction unit 101 as well as the weight measurement unit 2 and the connection cable 12 both of which are configured in the same manner as that of the first embodiment. The restriction unit 101 includes two frames 102 mounted to the lift unit 8, a flexible net or meshed sheet 103 secured to the frames 102 on which an animal is placed with four limbs passing through any four meshes of the net, freely settable electrodes 104, 104', 105, 105' that can freely be set to the roots of limbs of the animal while passing them through the meshes of the net 103, and an encoder 107 manually slid on a prior art encoder guide 106 while watching the same according to the distance between the front and rear legs of the animal.

It is noted, here, that the net 103 should have such size that is at least greater than the distance between the roots of front and rear legs of the animal or specimen.

Because the two frames 102 for securing the net 103 are supported by the lift unit 8 the spacing between the two frames 102 becomes narrower as the height of the lift unit 8 is raised.

The procedure for restriction of the animal according to the animal health care system 100 will be described in more detail. At first, an animal is placed on the net 103 with four limbs passing through any four meshes of the net according to the width and length between the limbs. In order to make four limbs of the animal floated off the floor or the weight measurement unit 2 the height of the lift unit 8 is increased via the operation unit 9. Accordingly, the spacing between the two frames 102 is gradually decreased until the animal placed on the net 103 becomes sandwiched at both sides between the frames 102, thereby completely restricting the animal in posture. It is assumed that the four limbs of the animal have sufficiently been floated at the time that the animal is restricted in such manner.

Then, the freely settable electrodes 104, 104', 105, 105' are set to the roots of the limbs, respectively. The electrodes 104, 104' are used for current supplying and the electrodes 105, 105' are used for voltage measurement. Because of nature of the freely settable electrode it can be set to the animal by sandwiching it between the root of the limb and the mesh of the net 103 that is contact to the animal body at the position near the root of the limb. While watching the position of the electrode that is set in this manner the encoder 107 on the encoder guide 106 is manually slid to set the distance between the front and rear legs of the animal. Now, the animal has been restricted in posture. Thereafter, the animal health care system 100 can be used to measure the impedance and to make judgment of adiposity of the animal in the same manner as that described with reference to FIGS. 7 to 9.

A third embodiment of the present invention is configured in such manner that, instead of using the impedance, the weight value estimated from the girth of trunk portion is compared to the actual measurement of weight and the rate of body composition is estimated based on the difference in weight value per same cross section area. Assuming that the body composition includes muscle and fat, the muscle is greater in weight per same cross section area. Accordingly, if weight value per same area is lighter then it is considered that the fat mass is greater.

Furthermore, the regression formula resulted from the correlation between the difference in weight value and the body fat rate actually measured is used to calculate the body fat rate and to make judgment of adiposity.

Figure 12:
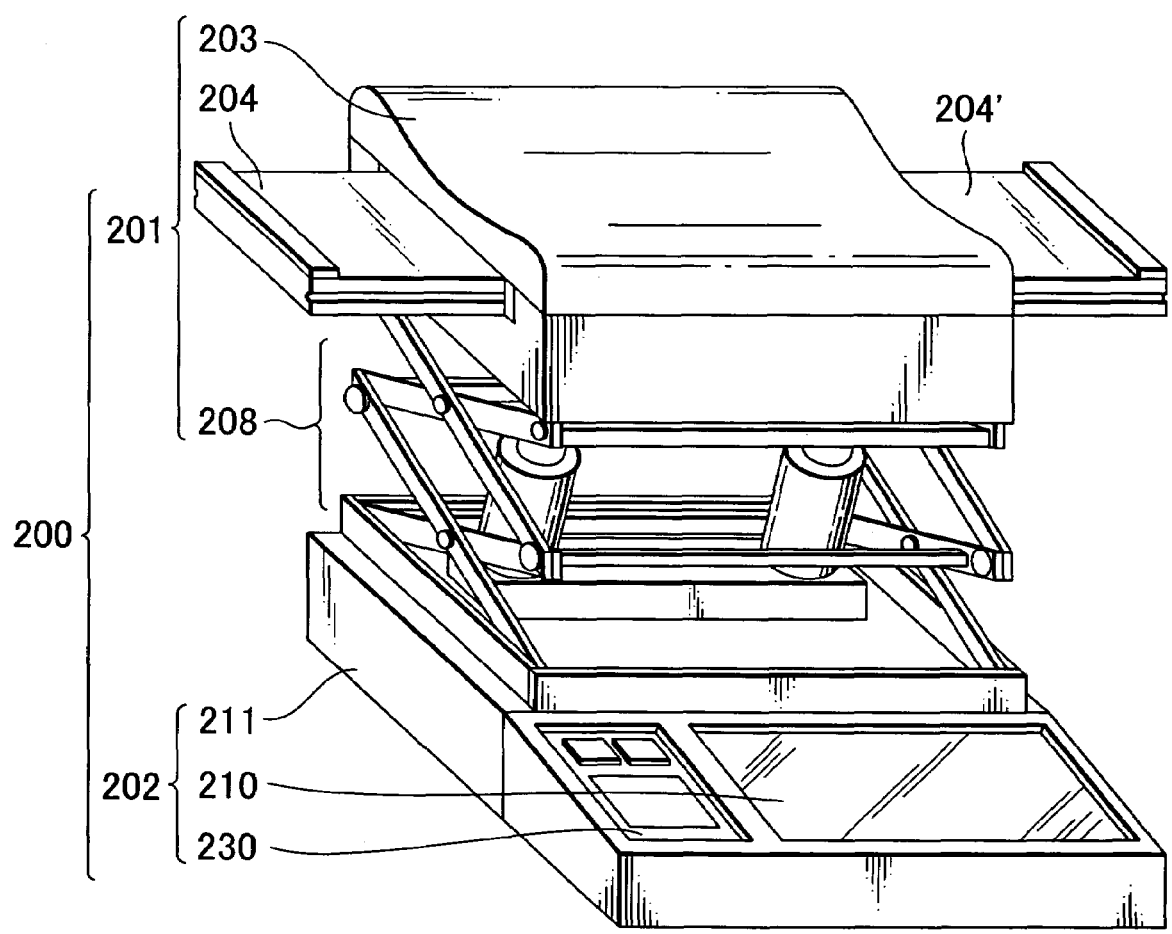
FIG. 12 is an external view of an animal health care system of third embodiment.

The third embodiment of the present invention will now be described in more detail with reference to FIG. 12, while comparing to the first embodiment as shown in FIGS. 1 to 4. FIG. 12 is an external view of a third embodiment of the present invention.

An animal health care system 200 of the third embodiment as shown in FIG. 12 is substantially same as the animal health care system 0 of the first embodiment, except that the electrodes 5, 5', 6, 6', the electrode slider 7, 7', the encoder 16 and the encoder guide 17 are omitted. Furthermore, the operation unit 9 in FIG. 1 is replaced by an operation and input unit 230 having ten-keys for numerically entering the morphologic measurement data of an animal. The configuration and mechanism of other components of the system 200 are same as that of the first embodiment, but in order to avoid any confusion, the components in the external view of FIG. 12 have different reference numerals: a restriction unit 201, a weight measurement unit 202, a platform 203, a front leg auxiliary support 204 and a rear leg auxiliary support 204', a lift unit 208, a display unit 210 and a scale 211.

Figure 13:
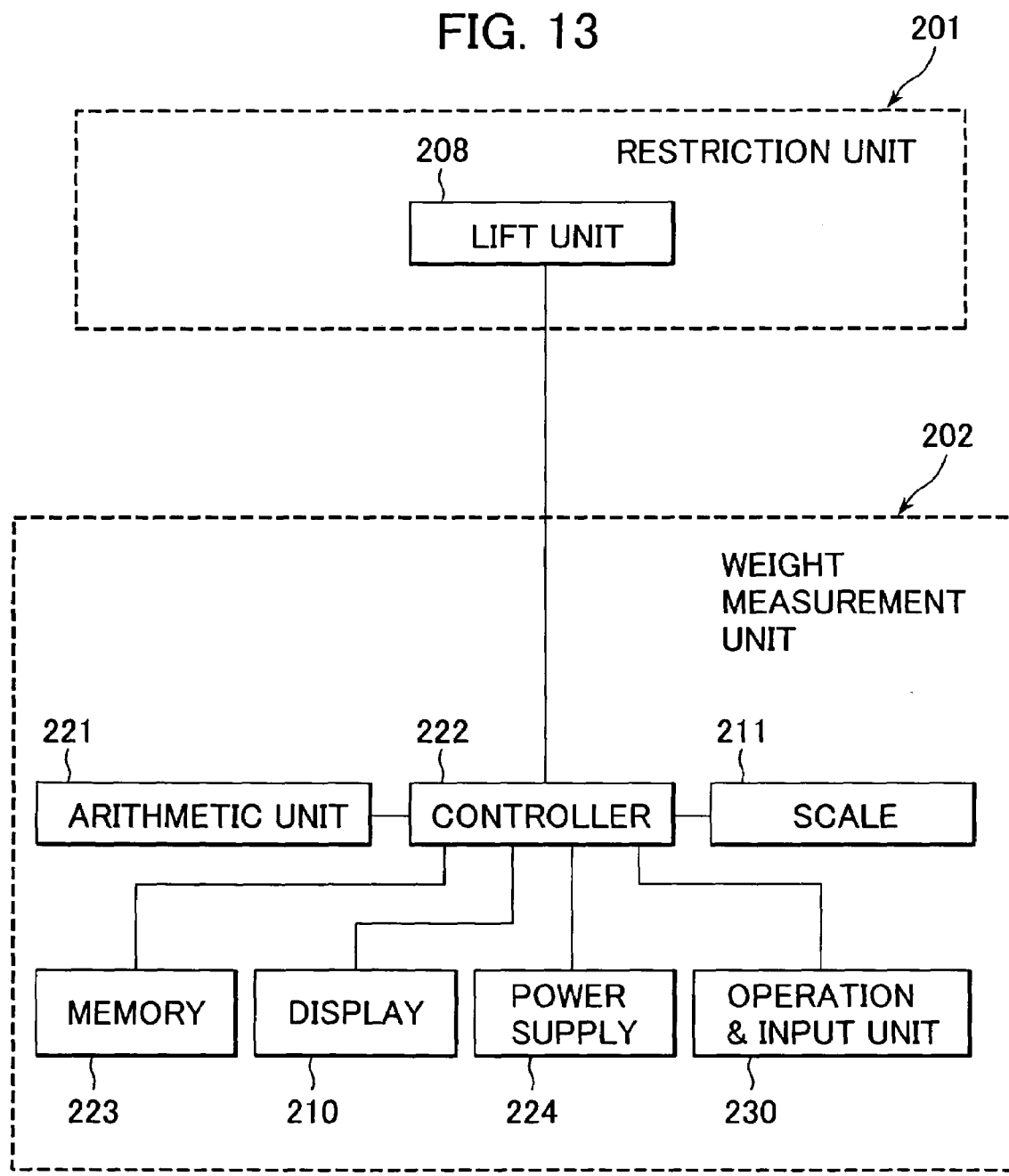
FIG. 13 is a functional block diagram of the third embodiment.

Now, referring to FIG. 13 that is a functional block view of the third embodiment, the internal functions in the animal health care system 200 will be described. In this system 200 the lift unit 208 of the restriction unit 201 is connected to a controller 222 in the weight measurement unit 202. In the weight measurement unit 202 the scale 211 for measuring the weight is connected to the controller 222 which is, then, connected to an arithmetic unit 221 for calculating the body fat rate from measurement data and for judging the adiposity. Furthermore, the controller 222 is connected to a memory 223 for storing measurement result and criterion for judgment of adiposity, a display unit 210 for displaying measurement data and result of judgment of adiposity, a power supply 224 for supplying power to the animal health care system 200, and an operation and input unit 230 for power supply switching, measurement operation, and numeric entering by ten-keys.

Figure 14:
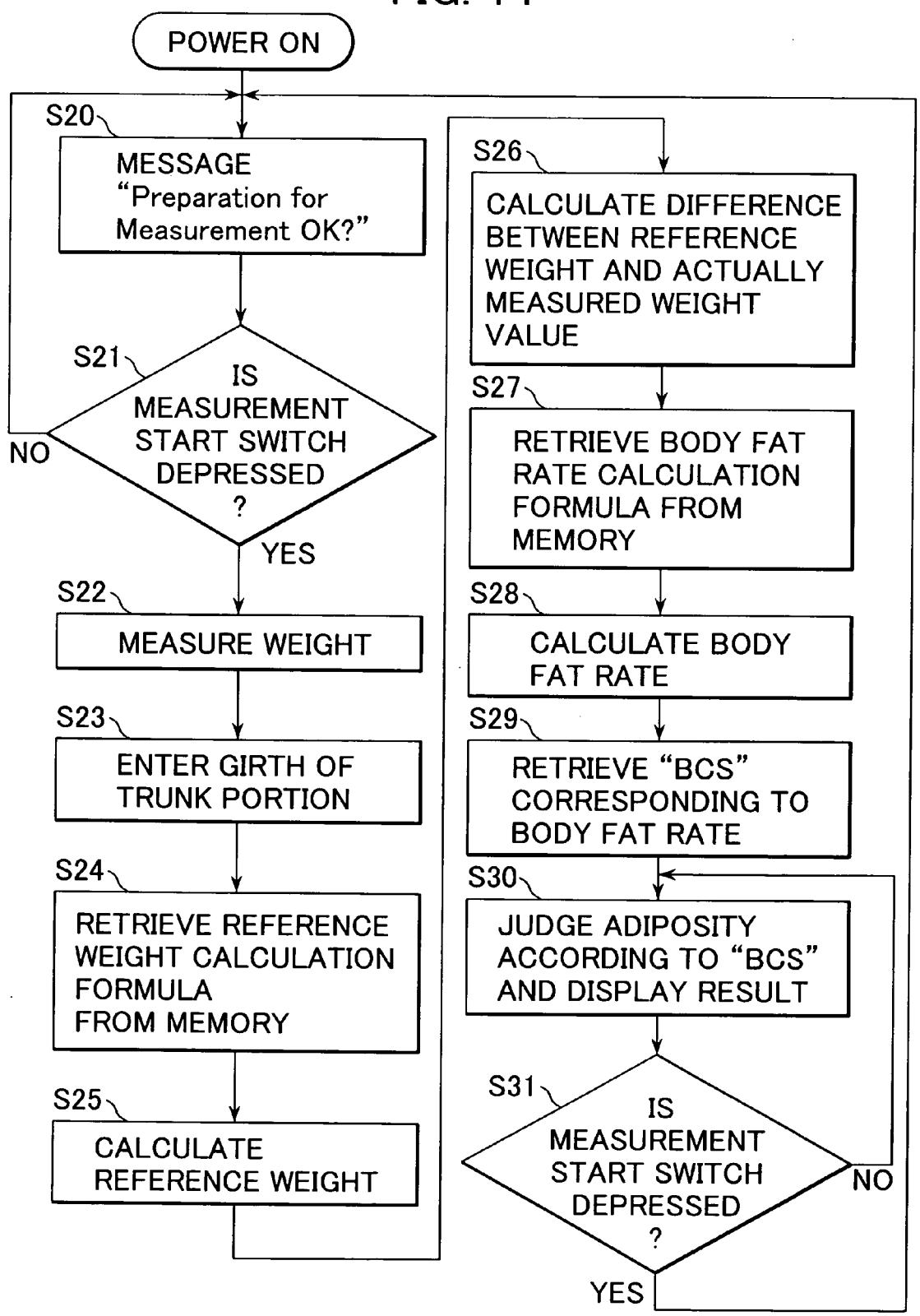
FIG. 14 is a flow chart illustrating an operation of the third embodiment.
Figure 15:
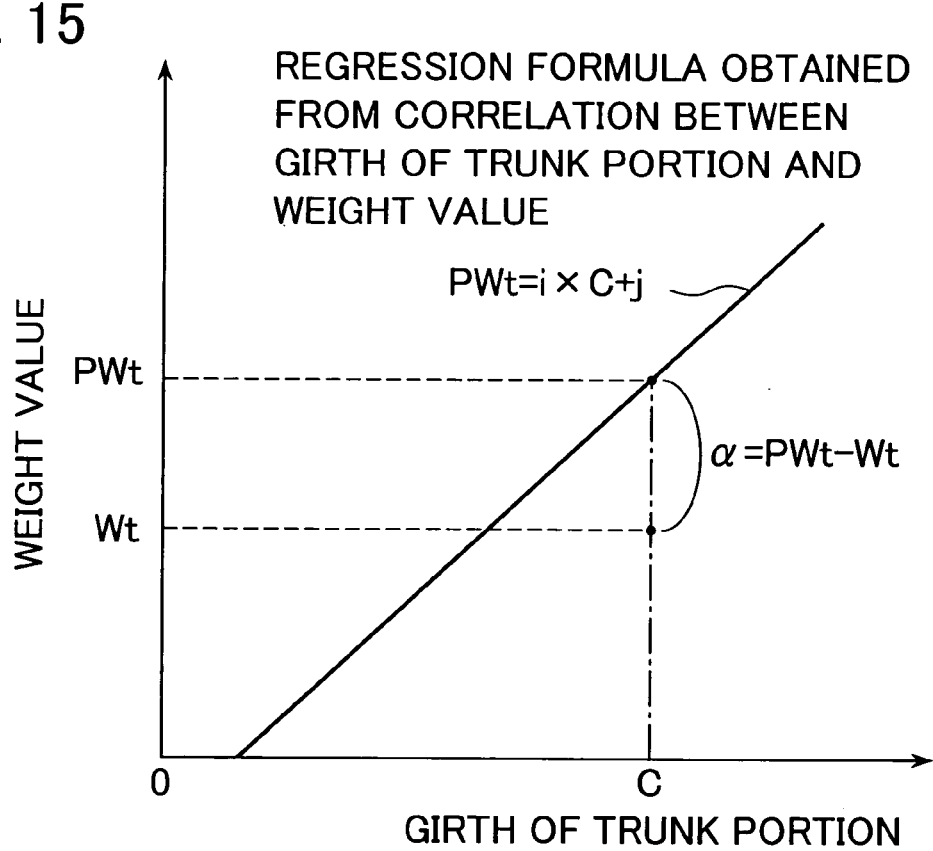
FIG. 15 is a graph showing relation between the girth of trunk portion and the weight value.
Figure 16:
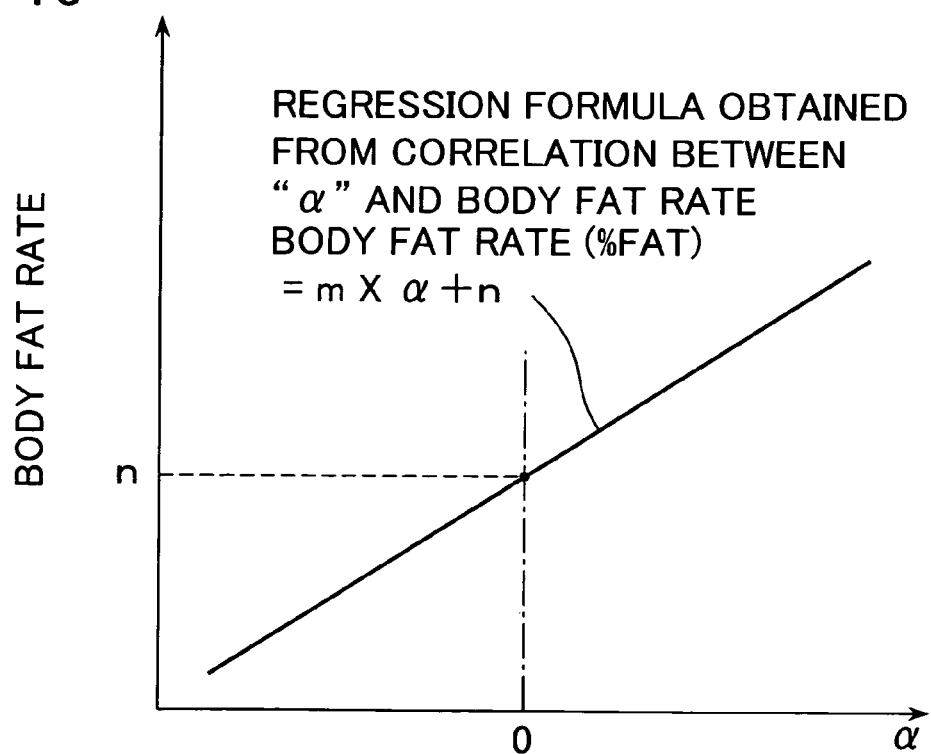
FIG. 16 is a graph showing relation between the body fat rate (% FAT) and the difference ($\alpha$) between reference weight value (PWt) and actually measured value (Wt).

One example of process for judging the adiposity of a dog as the specimen according to the animal health care system 200 configured as described above will be described in more detail with reference to FIGS. 14 to 16. In particular, FIG. 14 is a flow chart illustrating an operation of the animal health care system; FIG. 15 is a graph showing relation between the girth of trunk portion and the weight value; FIG. 16 is a graph showing relation between the body fat rate (% FAT) obtained by "TEXA" measurement and the difference between reference weight value and actually measured value.

Referring to the flow chart of FIG. 14, at first, the power switch on the operation and input unit 230 is depressed to turn ON the power supply for the animal health care system 200. Then, at step S20 in FIG. 14, a message is displayed for prompting to perform a preparation for measurement by restricting a dog in the restriction unit 201 as the specimen, and to push the measurement start switch on the operation and input unit 230 after the preparation for measurement has been done. Next, at step S21, a check is made to determine whether the measurement start switch on the operation and input unit 230 is depressed or not. If the answer is NO, the routine proceeds back to step S20 to once again display the message.

But, if the measurement start switch on the operation and input unit 230 is depressed according to the above message and the answer on the decision step S21 is YES then the measurement for the dog is started.

At step S22 the weight value of the dog restricted in the restriction unit 1 is measured by the weight measurement unit 202. Then, at step S23, the girth of trunk portion of the dog as measured by a measuring tool, etc., in advance is entered using the ten-keys on the operation and input unit 230.

At step S24 the regression formula for estimating the weight value from the correlation between the girth of trunk portion and the weight value is retrieved from the memory 223. Then, at step S25, the weight value is calculated from the girth of trunk portion that is entered as described above according to the regression formula, and the calculated weight value is stored in memory 223 as the reference weight value.

At step S26 the difference between the reference weight value and the actually measured weight value provided at step S22 is calculated. FIG. 15 is a graph illustrating the relation between the girth of trunk portion and the weight value of the animal. In this figure "C" is the girth of trunk portion and "PWt" is the reference weight value resulted from the regression formula which is then obtained from the correlation between the girth of the trunk portion and the weight value. The regression formula is written by:

$$PWt = i \times C + j$$

where "i" and "j" are constant. Furthermore, "Wt" is an actually measured value and "α" is the difference "PWt−Wt" between the reference weight value and the actually measured value.

The difference "α" means that there is difference in weight per same girth of trunk portion or same cross-section area. That is to say, it is considered that there is different rate of muscle to body fat mass as compared to the body composition at the time of reference weight value "PWt". Namely, if the actually measured value "Wt" is lighter than the reference weight value "PWt" it means that there is greater amount of body fat mass for the case of the actually measured value "Wt" as compared to the rate of muscle to body fat rate for the case of the reference weight value "PWt". In other words, it can be said that the body fat rate is higher.

Accordingly, at step S27, the body fat rate calculation formula stored in the memory 223 is retrieved to calculate the body fat rate based on the difference "α". The body fat rate calculation formula is such regression formula that is obtained from the correlation between the difference "α" and the body fat rate of the animal as calculated according to the prior art "DEXA" measurement in advance. FIG. 16 is a graph showing the relation between "α" and the body fat rate. For example, the regression formula is written by:

$$\text{Body Fat Rate (\% FAT)} = m \times (PWt - Wt) + n$$

where "m" and "n" are constant.

Steps S29, S30 and S31 are equal to steps S10, S11 and S12 in the first embodiment as shown in the flow chart of FIG. 7 in which the judgment for adiposity according to "BCS" is performed and the result of judgment is displayed.

As described above, at step S23, the girth of trunk portion is measured by the measuring tool and the like in advance because it is numerically entered by the operation and input unit 230. Alternatively, because the trunk portion is the maximum sized portion of the main body of the animal the platform 203 or each auxiliary support 4, 4' may be provided with any prior art measuring tool which is drawn to measure the girth of trunk portion after the animal is restricted. In addition, if the prior art encoder is used as the measuring tool the measurement and subsequent numerical input operation can automatically be done, instead of manually entered via the operation and input unit 230.

As also described above, at step S25, the reference weight value is calculated only from the girth of trunk portion. Alternatively, the morphologic data such as the body length, body height, distance between front and rear legs, etc., may be taken into account for calculation of the reference weight value. In such case, the more precise reference weight value can be produced because any kind of animals which are difficult to judge simply on the girth of trunk portion can properly be handled. In particular, if the animal is dog, such kind of dogs that have same girth of trunk portion, but longer in body length or that are large sized, but slender in body build having the girth of trunk portion equal to that of small sized dogs can properly be handled.

Furthermore, the body fat rate may directly be calculated from the morphologic measurement data using the regression formula that is obtained from the correlation between the morphologic information including the girth of trunk portion and the body fat rate of the animal calculated by e.g. "DEXA" measurement method in advance.

In the first to third embodiments, as described above, judgment for adiposity is performed by calculating the body fat rate using the regression formula or other prior art body fat rate calculation formula, then objectively estimating "BCS" based on the calculated body fat rate, and assessing the degree of adiposity with five ranks according to the estimated "BCS". Alternatively, the degree of adiposity may be assessed more finely than five ranks according to "BCS" so that more detailed judgment for adiposity can be attained.

Furthermore, it is not necessary that only one regression formula is used for all kinds of animals. For example, the animals may be classified into some kinds such as dogs, cats, etc., and then, e.g. dogs may further be classified into some classes such as large sized dogs, small sized dogs, etc. Then, a plurality of regression formulae each associated with each kind or class of the animal may be stored in the memory. Accordingly, it is possible to provide more exact health assessment data by selecting the kind or class of the animal that is the specimen for measurement. For example, in the first and second embodiments, as described above, a plurality of animal selection switches may be provided in the operation unit 9 for selecting the kind of animal and a check may be done at step S2 in FIG. 7 to determine whether any one of the animal switches is depressed, instead of the measurement start switch.

Furthermore, as described above, the height of the lift unit is adjusted to float the four limbs of the animal, thereby preventing the animal from acting violently. Alternatively, in the first embodiment, as described above, a fastening tool such as a belt for fastening the animal may be provided to the platform 3 or the auxiliary support 4, 4'.

Now, the present invention will be described with reference to a further embodiment in which the body build of dog affecting the body temperature is classified into a plurality of classes according to kinds of dogs, the correction factor for correcting the body temperature is set, and the metabolism of the dog when it is in rest condition is calculated based on the fat free mass of the dog by adding the correction factor as the correction term for body temperature. Furthermore, the energy consumption is calculated from the metabolism of the dog in rest condition and the action data of the dog, and the proper intake energy is calculated by taking into account of the degree of adiposity for the dog, which allows health care for each of dogs.

Figure 17:
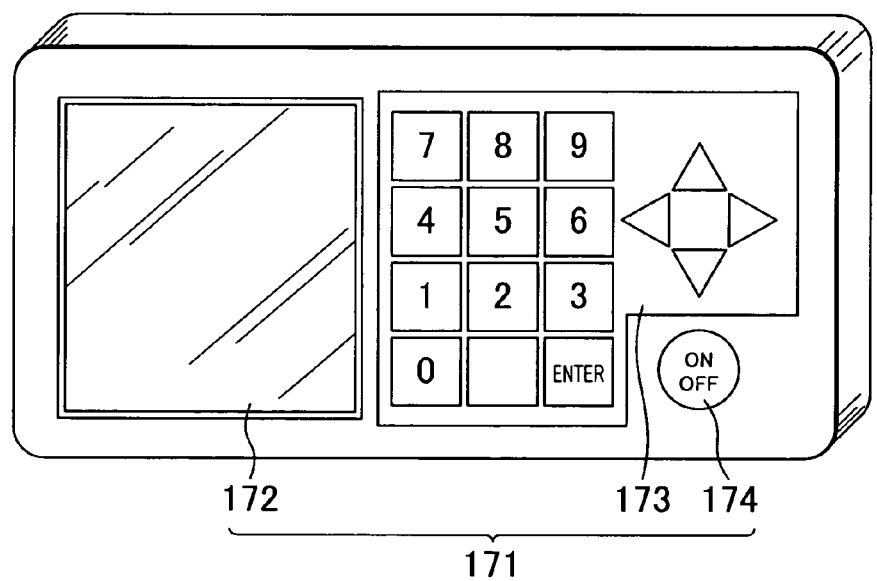
FIG. 17 is an external view illustrating a dog health care system according to a fourth embodiment of the present invention.
Figure 18:
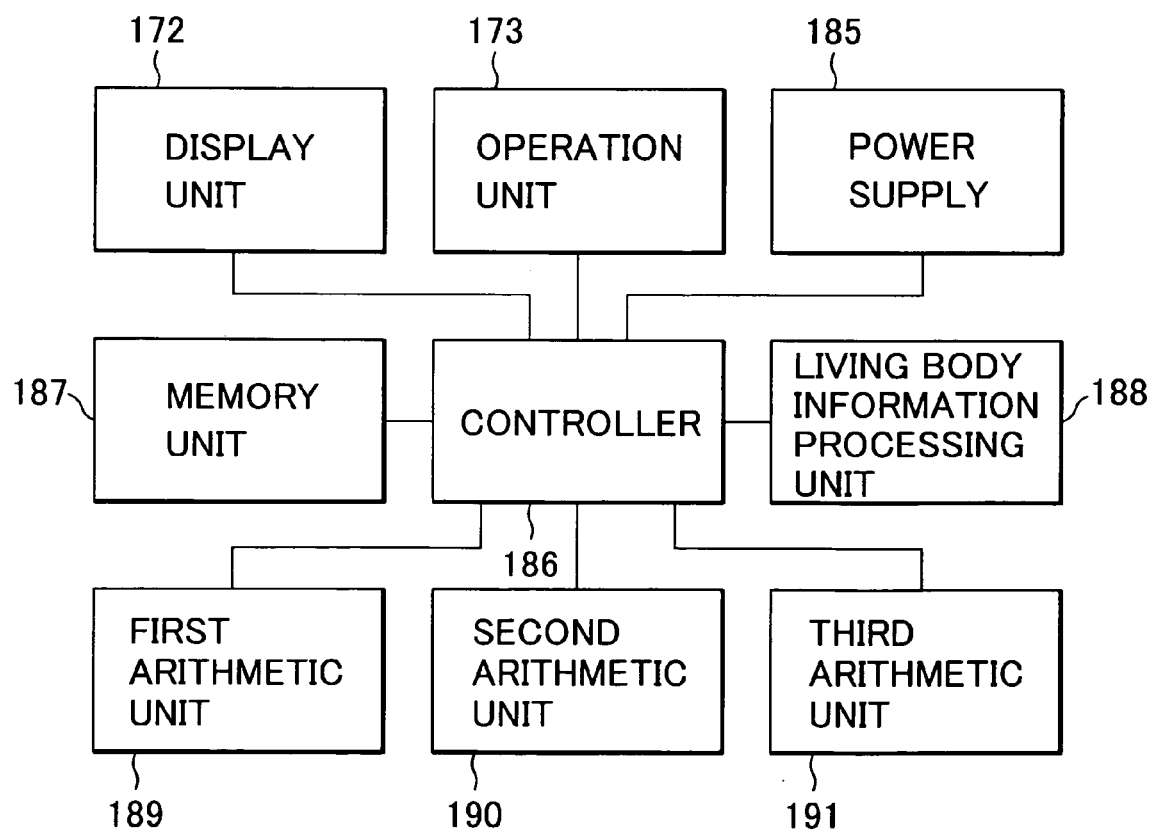
FIG. 18 is a functional block diagram of the dog health care system.

Referring now to FIGS. 17 and 18, a configuration of the embodiment of the present invention will be described. FIG. 18 is an external view of a dog health care system 171.

Referring to FIG. 17, a dog health care system 171 comprises a display unit 172 for displaying input data, each calculation result, etc., an operation unit 173 for selecting data and entering numerical value, and a power switch 174 for turning power supply ON and OFF.

FIG. 18 is a functional block diagram of the dog health care system 171. The display unit 172 and the operation unit 173 are connected to a controller 186. Also connected to the controller 186 are: a memory 187 for storing calculation formulae for calculating metabolism of a dog in rest condition, consumption and intake energy; and a living body information processing unit 188 for calculating fat free mass from the entered data and for judging the degree of adiposity of the dog. Further connected to the controller 186 are: a first arithmetic unit 189 for calculating the metabolism of the dog in rest condition from the entered data; a second arithmetic unit 190 for calculating the energy consumption from the metabolism in rest condition and an action data of the dog, and a third arithmetic unit 191 for calculating, based on the calculated energy consumption, proper intake energy or proper amount of food relative to target weight reduction, or energy consumption or exercise data necessary for weight reduction. In addition, a power supply 185 for supplying power to the dog health care system 171 is connected to the controller 186.

Figure 19:
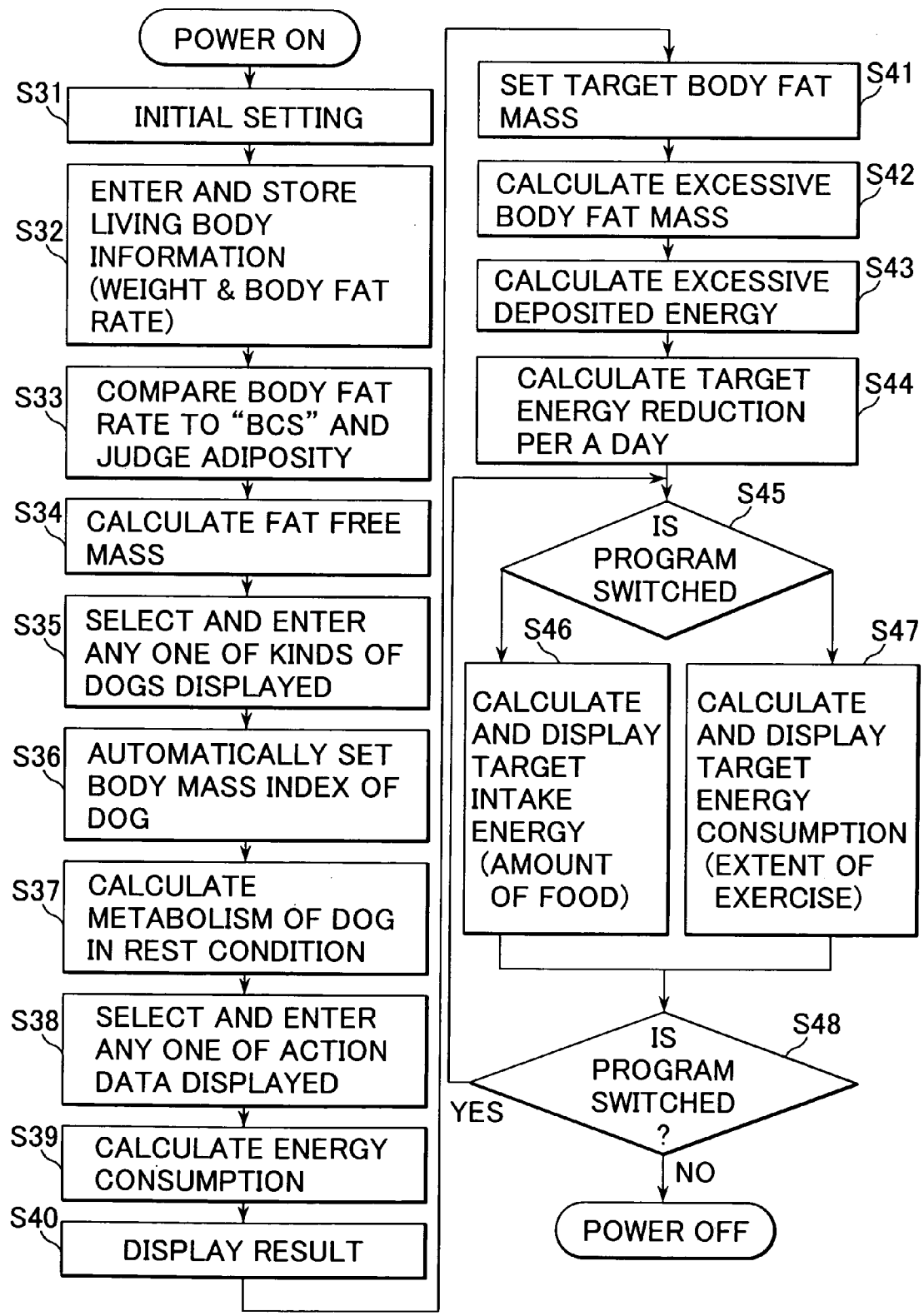
FIG. 19 is a flow chart illustrating operation of the dog health system.
Figures 22, 23:
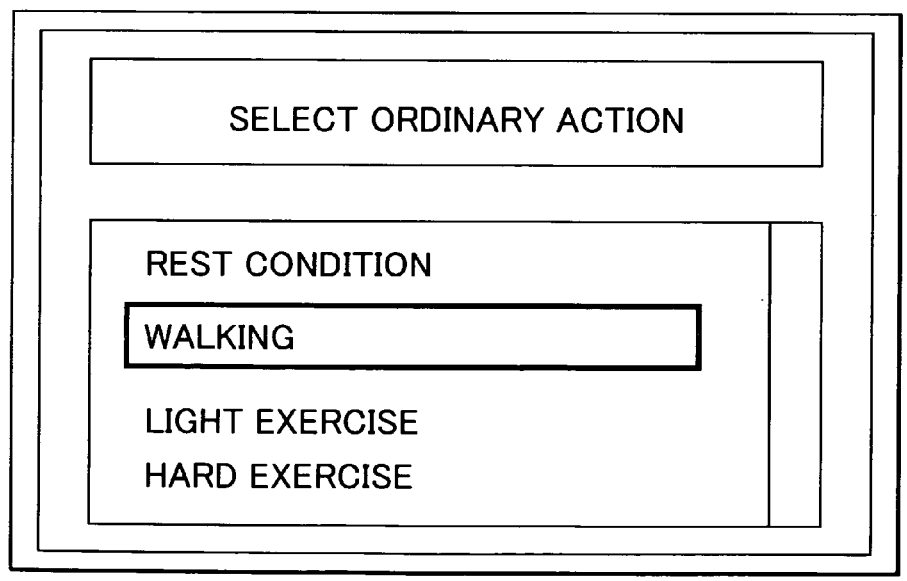
FIG. 22 is a table listing body temperature correction factors and the corresponding kinds of dogs.
FIG. 23 is a view illustrating further example of display screen.
Figures 24, 25:
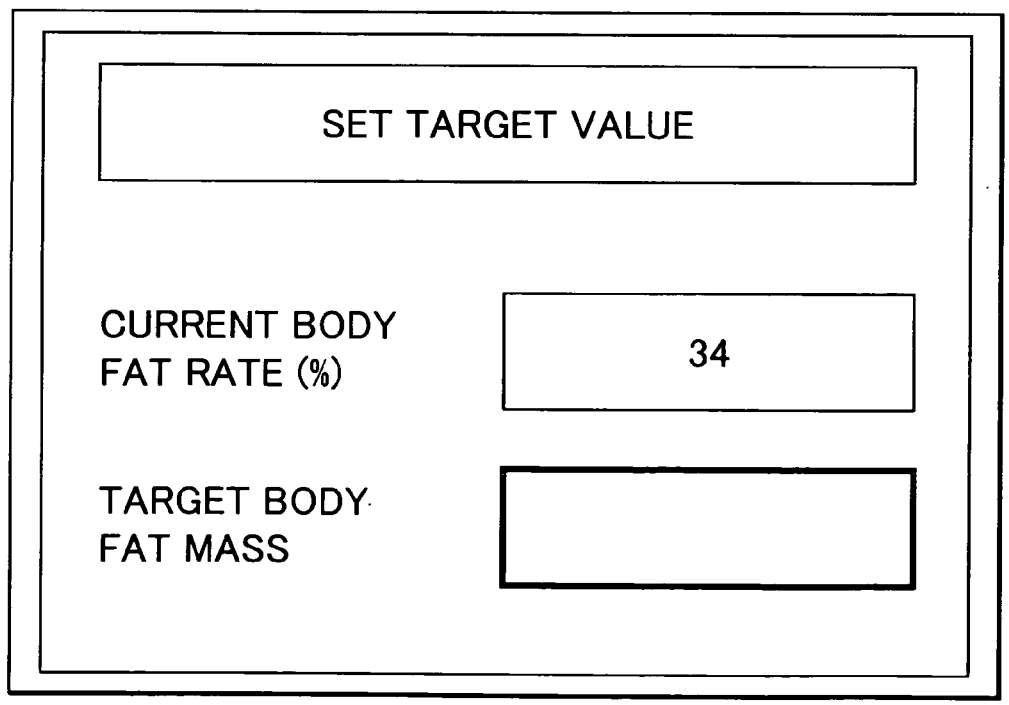
FIG. 24 is a table listing action level indices and the corresponding actions of dog.
FIG. 25 is a view illustrating yet further example of display screen.

Referring now to FIGS. 19 to 26, operation of the dog health care system according to the embodiment will be described in more detail. In particular, FIG. 19 is a flow chart illustrating entire operation of the system; FIGS. 20, 21, 23, 25 and 26 show examples of display each illustrating each operation of the system; FIG. 22 is a table listing body temperature correction factors classified according to kinds of dogs; and FIG. 24 is a table listing action level indices for dog.

Referring first to the flow chart of FIG. 19, operation of the system is started by turning ON the power switch 174 in FIG. 17. At step S31 an initial setting is done and at step S32 a data input screen for entering the weight value and the body fat rate is displayed on the display unit 172, as shown in FIG. 20, together with a message for prompting to enter the living body information. In response to the message, a measurement person operates the operation unit 173 to sequentially enter the weight value and the body fat rate as measured by any measuring instrument in advance and depresses an enter key each time the correct number is set to store it in the memory unit 187.

The measuring instrument, as described above, may be configured in such manner that a dog is set with its chest and abdomen region positioned on the instrument while floating its four limbs off the floor for weight measurement, impedance measurement electrodes are made contact to the roots of four limbs to measure the impedance between front and rear legs and distance between the electrodes, and a morphologic model of main body of the dog is created from the weight value, impedance value and distance between the electrodes for calculating the body fat rate, as in the case of calculation of body fat rate for a human.

At step S33 the controller 186 retrieves "Body Condition Score" (hereafter referred to as "BCS") which is prior art criterion for judgment of adiposity of dog and is stored in the memory 187. Then, the living body information processing unit 188 selects the score range of "BCS" corresponding to body fat rate entered and judges the degree of adiposity, the result of which is stored in the memory 187. At step S34 the fat free mass is calculated from the weight value and the body fat rate. In particular, the living body information processing unit 188 calculates the body fat mass (kg) by the following formula:

Body Fat Mass (kg)=Weight Value (kg)×Body Fat Rate (%)

and then calculates the fat free mass (kg) by the following formula:

Fat Free Mass (kg)=Weight Value (kg)−Body Fat Mass (kg)

The calculated body fat mass and fat free mass are each stored in the memory unit 187.

At step S35 the controller 186 retrieves the information about several kinds of dogs stored in the memory unit 187 in advance and displays it on the display unit 172 in a table listing the kinds of dogs, together with a message for prompting to select and enter the kind of dog, as shown in FIG. 21. In response to the message the measurement person selects and enters the kind of the dog that is the specimen via the operation unit 173. At step S36 the body temperature correction factor corresponding to the kind of dog selected is automatically retrieved from the memory 187. The body temperature correction factors each corresponding to each of kinds of dogs are listed in the table of FIG. 22, by way of an example.

The body temperature correction factor is provided for the purpose of correcting the body temperature of the dog that is varied depending on the kinds of dogs, and the body temperature correction factor is predetermined based on the body build of the dog affecting its body temperature and the body hair level exhibiting thermal insulation effect. In particular, the body temperature depends on the body build so that the smaller sized dog has relatively higher temperature while the larger sized dog has lower temperature. Accordingly, the average weight for each kind of dogs is compared to others to classify the dogs according to their body build. For example, a Chihuahua having the lowest average weight is considered as the reference and other dogs are classified according to the value of the average weight for each kind of dogs divided by the average weight of the Chihuahua. If the same kind of dogs have the different average weight depending on whether it is male or female then they are differently classified. Furthermore, because of the dogs having longer hair providing higher thermal insulation effect even within the same kind the dogs are also classified according to the body hair type. The number expressing the classification of dogs for each kind is the body temperature correction factor.

Then, at step S37 the calculation formula for calculating the metabolism of the dog in rest condition is retrieved from the memory 187. The calculation formula for calculating the metabolism of the dog in rest condition is such regression formula that is obtained from the multiple correlation between the metabolism in rest condition resulted from analysis of expiration of the dog in rest condition, the fat free mass and the body temperature correction factor. For example, it is expressed by:

Metabolism in Rest Condition (kcal)=$a+b$×(Fat Free Mass (kg))+$c$×(Body Temperature Correction Factor According to Kind of Dog)

where "a", "b" and "c" are constant. In the first arithmetic unit 189 the fat free mass calculated and the body temperature correction factor selected according to the kind of dog entered are substituted for the calculation formula for calculating the metabolism in rest condition.

At step S38 the action data having predetermined several action steps is retrieved from the memory 187 and is displayed on the display unit 172, as shown in FIG. 23, together with a message for prompting to select and enter the action data. In response thereto the measurement person selects and enters the action data via the operation unit 173. The action data is represented by action indices each indicating the ordinary action of the dog classified into plural steps, as shown in FIG. 24. In particular, the action indices are shown as the scale factors for four ordinary actions from "Rest Condition" to "Hard Exercise" assuming that the scale factor for the rest condition is 1.

Next, at step S39 the energy consumption calculation formula is retrieved from the memory 187. In the second arithmetic unit 190 the metabolism in rest condition calculated and the action data entered are substituted for the formula to calculate the energy consumption. The energy consumption calculation formula is written by:

Energy Consumption (kcal)=(Metabolism in Rest Condition (kcal))×(Action Data)

Then, at step S40 the weight value, body fat rate, body fat mass, fat free mass, degree of adiposity, kind of dog, metabolism in rest condition and energy consumption is displayed on the display unit 172 as the measurement result.

At step S41 a message is displayed for prompting to enter the target body fat rate associated with the target weight reduction, as compared to measurement result displayed, as shown in FIG. 25. In response to the message the measurement person enters the target body fat rate via the operation unit. Then, in the third arithmetic unit 191, the target body fat mass is automatically calculated based on the target body fat rate and the current weight value, and the calculated target body fat mass is stored in the memory 187.

Next, at step S42 an excessive body fat mass is calculated, which means the difference between the current body fat mass and the target body fat mass, that is to say, the part of body fat mass to be reduced. At step S43 the third arithmetic unit 191 calculates the energy deposited in the excessive body fat mass. In general, it is well known that the energy of 7.2 (kcal) is deposited per a body fat mass of 1 (g). Therefore, the excessive deposited energy is calculated by the following formula:

Excessive Deposited Energy (kcal)=Excessive Body Fat Mass (g)×7.2 (kcal/g)

Then, at step S44 in order to reduce the excessive deposited energy the third arithmetic unit 191 calculates target energy reduction per a day. For weight reduction it is generally considered preferable that the weight reduction is within 5% of the weight per a month. Assuming that the target reduction is set at 5% of the weight per a month the target reduction per a day is written by the following formula:

Target Weight Reduction per a Day (g/day)=Weight Value (g)×(5/100)/30

In order to reduce the body fat mass corresponding to this target weight reduction the target energy reduction per a day is written by the following formula:

Target Energy Reduction per a Day (kcal/day)=Target Weight Reduction per a Day (g/day)×7.2 (kcal/g)

Then, based on the target energy reduction per a day, the number of days to attain the target body fat mass is calculated by the following formula:

Target Number of Days (days)=Excessive Deposited Energy (kcal)/Target Energy Reduction per a Day (kcal/day)

At step S45 the next weight reduction program is selected so that:

Target Energy Reduction per a Day (kcal)=Intake Energy (kcal)−Consumption Energy (kcal)

In this embodiment there are two weight reduction programs selectable: one is the program of reducing intake energy due to diet; and another is the program of increasing energy consumption due to increase in exercise. The person selects either one of those two programs displayed on the display unit 172 via the operation unit 173.

If the program of reducing intake energy is selected, at step S46, the energy consumption calculated at step S40 is retrieved from the memory 187 and the third arithmetic unit 191 calculates the intake energy based on the energy consumption and the target energy reduction by the following formula:

Intake Energy (kcal)=Energy Consumption (kcal)−Target Energy Reduction per a Day (kcal)

Then, at step S48 the result of calculation is displayed, together with the target number of days. Furthermore, more concrete amount of pet food corresponding to the intake energy calculated, e.g. one package of food, is displayed.

On the other hand, if the program of increasing the energy consumption is selected, at step S47, a message for prompting to enter the amount of food that the dog actually ate in a day is displayed on the display unit 172. After the person enter the intake energy of the food via the operation unit 173 then the third arithmetic unit calculates the energy consumption based on the intake energy and the target energy reduction per a day by the following formula:

Energy Consumption (kcal)=Intake Energy (kcal)−Target Energy Reduction per a Day (kcal)

Then, at step S48 the result of calculation is displayed, together with the target number of days. Furthermore, more concrete exercise data corresponding to the energy consumption calculated, e.g. "30-minute walk", is displayed using the predetermined relation between the energy consumption and the exercise data.

At step S48 a check is made by the controller 186 to determine whether the program is switched and selected once again. If the program is switched by depressing some specified button, for example, then the routine returns to step S45 so that either of the operations associated with the programs is executed, as described above. On the other hand, if no switching of the program is done the answer of step S48 is "NO" and the power supply 185 is turned OFF to end the operation of the system.

Instead of the body temperature correction factor according to the kind of dogs, as described above, such body temperature correction factor may be used that is derived from the body build of the dog according to its weight value entered, as shown in FIG. 26. In this case, after entering the amount of body hair affecting the body temperature and the body hair type data such as longer hair, shorter hair, etc., in addition to this body temperature correction factor, the first arithmetic unit 189 can calculate the metabolism in rest condition, in the same manner as above, using the regression formula that is obtained from the multiple correlation between the metabolism in rest condition resulted from analysis of expiration of the dog in rest condition, the body temperature correction factor according to weight value, and the amount of body hair or body hair type data. For example, the regression formula is written by:

Metabolism in Rest Condition (kcal)=$d$+$e$×(Fat Free Mass (kg))+$f$×(Body Temperature Correction Factor According to Weight Value)+$g$×(Amount of Body Hair)

where "d", "e", "f" and "g" are constant.

Accordingly, even the crossbred dogs which are difficult to be classified can be measured. Furthermore, if the metabolism in rest condition is calculated by taking into account of this body temperature correction factor according to the weight value, in addition to the body temperature correction factor according to the kind of dogs, as described above, even the dogs of the same kind but clearly different in body build can be classified as to whether it is a puppy or a grownup. Therefore, the accuracy with which the metabolism in rest condition is measured can be improved.

Moreover, if the age of the dog in years or months is entered the dogs can more precisely be classified from a puppy to a grownup, in addition to the classification according to the kind of dogs. Then, the metabolism in rest condition can be calculated with higher precision by taking into account of the age of the dog in years or months.

In the embodiment, as described above, the fat free mass calculated from the weight value and the body fat rate is used for the fat free data. However, by using the amount of muscle instead of the fat free mass the metabolism in rest condition can be calculated with higher precision because the muscle is such living body organization that generates heat.

The weight value and body fat rate numerically entered via the operation unit 173 at step S32 in FIG. 19 is such data that has been measured by the measuring instrument in advance, as described above. Alternatively, the above measuring instrument may be connected to the dog health care system so that the data is directly transmitted thereto. Furthermore, instead of using the measuring instrument for calculating the body fat rate due to the impedance method, an estimation of body fat rate based on judgment of adiposity according to "BCS", for example, may be used. Otherwise, the body fat rate estimated using the regression formula resulted from the correlation between the body fat rate and the morphologic measurement data such as the girth of trunk portion, body length, etc., of the dog may be used.

Because the body fat rate is the value exhibiting suppression of heat radiation and also exhibiting adiabatic effect for heat deposition in the body then the first arithmetic unit 189 can calculate the metabolism in rest condition, in the same manner as above, using the regression formula that is obtained from the multiple correlation between the metabolism in rest condition resulted from analysis of expiration of the dog in rest condition, the body temperature correction factor according to the kind of dogs, and the body fat rate. Accordingly, the metabolism in rest condition can be calculated by taking into account of the degree of adiposity. For example, the regression formula is written by:

Metabolism in Rest Condition (kcal)=$h$+$i$×(Fat Free Mass (kg))+$j$×(Body Temperature Correction Factor According to Kind of Dog)+$k$×(Body Fat Rate(%))

where "h", "i", "j" and "k" are constant.

Although at step S37 in FIG. 19 the first arithmetic unit 189 calculates the metabolism in rest condition, as described above, it may calculate the basal metabolism. For example, the correlation between the analysis data of expiration of the dog during the fixed interval from waked up after putting it to sleep with anesthesia, for example, the fat free mass, and the body temperature correction factor according to the kind of dogs may be used to derive the regression formula which is then stored in memory 187 as the basal metabolism calculation formula for calculating the basal metabolism.

At step S38 any one of the action indices associated with the ordinary actions of the dog classified by plural steps is selected and entered for the action data, as described above. Alternatively, some exercise monitoring device for measuring the exercise of dog such as a pedometer, an accelerator, etc., may be used to determine the extent of exercise which is then manually entered into the dog health care system or the exercise monitoring device may be connected to the dog health care system for directly data communication. Then, the second arithmetic unit 190 calculates the energy consumption due to the exercise.

Furthermore, at step S39 in FIG. 19 the second arithmetic Unit 190 calculates the energy consumption based on the metabolism in rest condition and the action data, as described above. Because of some energy consumed under ambient temperature, by entering the ambient temperature and adding the correction term according to the ambient temperature to the energy consumption calculation formula, more precise energy consumption can be resulted. The energy consumption calculation formula is written by:

Energy Consumption (kcal)=Metabolism in Rest Condition (kcal)×(Action Data)×t×(Normal Temperature−Ambient temperature)$^2$ where "t" is constant. The ambient temperature may be set in advance for every season or every month so that it may be automatically entered as the correction term when the energy consumption is calculated.

In addition, at step S41 in FIG. 19 the measurement person numerically enters the target body fat rate via the operation unit 173, as described above. Alternatively, the standard value or the proper value for the body fat rate may automatically be set as the target value. For example, for the ideal body build according to "BCS" the body fat rate is in the range of 15 to 24%. Therefore, the target body fat rate may be set at 24% and the body fat mass corresponding thereto may automatically be set as the target body fat mass.

Moreover, at steps S45 to S48 in FIG. 19 either one of the two weight reduction programs: one for reduction in intake energy; and the other for increase in energy consumption is selected, as described above. If the ratio of selection of either one among two programs is predetermined then balancing between weight reduction due to exercise and that due to diet can be taken.

It is apparent from the foregoing that an animal health care system according to the present invention comprises: a weight input unit; an impedance measurement unit; an inter-leg distance input unit; and a health assessment data calculation unit, wherein said weight input unit enters weight value of an animal, said impedance measurement unit includes impedance measurement electrodes each for contacting with a root of each leg of the animal and measures impedance between front and rear legs of the animal, said inter-leg distance input unit enters the distance between the roots of front and rear legs of the animal, and said health assessment data calculation unit calculates health assessment data based on the weight value of the animal, the impedance between front and rear legs of the animal, and the distance between the roots of front and rear legs of the animal. Accordingly, unlike the prior art system in which the body length of the animal is used instead of the distance between impedance measurement points, it becomes possible to precisely measure the impedance of main body portion of the animal, thereby enabling health care of the animal with higher precision health assessment data. Furthermore, because impedance measurement is performed at the roots of four limbs where there is less body hair, contact resistance due to body hair is lower, which realizes stable impedance measurement.

The impedance measurement electrode is formed from flexible electrically conductive material such as electrically conductive resin, electrically conductive rubber, etc., or it comprises an electrically conductive member having a spherical portion or a spring-like portion formed thereon for contacting with the skin of the animal. Accordingly, it allows impedance measurement without any pain or any strong stimulation to the roots of four limbs of the animal to which the electrodes are made contact.

The impedance measurement electrode has a plurality of projected portions formed on the surface thereof for making sure to contact with the skin of the animal irrespective of presence of body hear. Accordingly, the projected portions on the electrode thrust through the body hair to surely contact to the skin of the animal.

The impedance measurement electrode has a cushion material such as sponge, cloth, etc., provided on the surface thereof for providing water-keeping capability. Accordingly, the cushion material is directly contact to the skin of the animal, which gives less stimulation to the animal. In addition, because of water included in the cushion, the electrode is contact to the skin of the animal via the water of which electrical conductivity is extremely higher. Therefore, impedance measurement can be done even using an electrode having a flat surface without degrading the precision for measurement and without any substantial effect by the body hair.

The impedance measurement electrode includes a constant pressure unit for producing constant pressure to make contact with the animal at the level of not stimulating the animal. Accordingly, because of no further force greater than necessary applied to the portions of the animal where the electrodes are mounted even under the condition that the body pressure of the animal is applied to the roots of four limbs thereof the impedance measurement can be done without any pain or any strong stimulation to the animal.

The health assessment data calculation unit calculates the health assessment data by taking into account of at least one of morphologic measurement data including body length, body height, girth of trunk, girth of chest or girth of waist of the animal. Accordingly, more precise morphologic model for an animal can be produced for deriving the health assessment data with higher precision.

The weight input unit includes a restriction unit by which at least one of the chest, abdomen, legs and roots of legs of the animal is placed and kept in position, and measures and enters the weight of the animal while restricting it in such manner that no legs of the animal are contact with those other than the restriction unit. Accordingly, the animal is restricted in posture under natural condition while standing on all four legs, but spaced away from the floor or the measurement system. Then, the animal is prevented from acting violently because of no power applied to the limbs, which contributes to smoothly measure the weight of the animal.

The restriction unit includes contact portions each for contacting with the root of each leg of the animal, and automatically measures and enters the distance between the contact portions, thereby also acting as the inter-leg distance input unit. Accordingly, simply by restricting the animal the distance between the roots of legs can also be measured.

The restriction unit includes contact portions each for contacting with the root of each leg of the animal and each provided with the impedance measurement electrode, thereby also acting as the impedance measurement unit. Accordingly, while the animal is restricted the measurement of impedance can also be done.

In another aspect of the present invention the animal health care system comprises: a weight input unit; an estimated weight calculation unit; and a health assessment data calculation unit, wherein said weight input unit enters weight value of an animal, said estimated weight calculation unit calculates an estimated weight value based on at least girth of the trunk of the animal among the morphologic measurement data such as girth of the trunk, body length and body height of the animal, and said health assessment data calculation unit calculates health assessment data based on the difference between the weight value and the estimated weight value. Accordingly, estimation of body fat rate of the animal can be done only from the morphologic measurement data and the weight value.

The weight input unit includes a restriction unit by which at least one of the chest, abdomen, legs and roots of legs of the animal is placed and kept in position, and measures and enters the weight of the animal while restricting it in such manner that no legs of the animal are contact with those other than the restriction unit. Accordingly, the animal is restricted in posture under natural condition while standing on all four legs, but spaced away from the floor or the measurement system. Then, the animal is prevented from acting violently because of no power applied to the limbs, which contributes to smoothly measure the weight of the animal.

The restriction unit has its width or height for receiving the animal, which can be adjusted according to the size of the animal. Accordingly, the restriction unit can restrict any of animals irrespective of its kind and size.

The restriction unit includes a flexible net or meshed sheet through which at least four limbs of the animal can pass, and frames for securing the net at any condition from spread condition to folded condition. Accordingly, different meshes of the net can be used to pass through the limbs of the different sized animals according to the dimension thereof, thereby facilitating the restriction of the animal.

The health assessment data calculated by the health assessment data calculation unit is at least one of body water mass, fat free mass and body fat rate of the animal. Accordingly, the animal health care can successfully be performed, as in the case of human being.

The health assessment data calculation unit includes a "BCS" (Body Condition Score) estimation unit for estimating "BCS" based on the health assessment data calculated. Accordingly, it is possible to easily determine "BCS" at home based on some objective index without any experience of an ocular inspection or a palpation by a veterinary or a specialist.

The health assessment data calculation unit includes an adiposity judgment unit for judging the degree of adiposity of the animal based on the health assessment data calculated. Accordingly, the adiposity judgment can easily be performed so that the animal health care can conveniently be done even at home.

Furthermore, an animal health care system according to the present invention comprises: a fat free data input unit; a body temperature related data input unit; a body temperature correction factor derivation unit; and a metabolism calculation unit, wherein said fat free data input unit enters fat free data of a dog, said body temperature related data input unit enters body temperature related data of the dog, said body temperature correction factor derivation unit derives body temperature correction factor based on said body temperature related data, and said metabolism calculation unit calculates metabolism of the dog based on said fat free data and said body temperature correction factor. Accordingly, the metabolism for each of dogs can be calculated.

The fat free data is fat free mass or amount of muscle, which may be derived from weight value and body fat data. Accordingly, more precise metabolism can be derived based not only on weight value, but also on living organization for heat generation.

The body temperature related data is at least one of the following: kind of dog and body build of dog. Accordingly, correction of body temperature can easily be done according to the size of dog without measurement of body temperature, which allows calculation of metabolism with higher precision.

The body build of dog is body mass index estimated from the weight value. Accordingly, the body build of dog can be classified according to the weight value, and therefore, calculation of body temperature correction factor based on the body build can easily be done.

The metabolism calculation unit includes a body hair data input unit for entering body hair data of the dog, and calculates the metabolism of the dog by taking into account of the body hair data entered thereby. Accordingly, the metabolism can be calculated with higher precision by taking into account of the effect of thermal insulation due to body hair.

The metabolism calculation unit includes an age input unit for entering the age of the dog, and calculates the metabolism of the dog by taking into account of the age. Accordingly, the metabolism of dog can be calculated with more precisely classified from a puppy to a grownup.

The metabolism calculation unit includes a thermal insulation effect factor derivation unit for deriving thermal insulation effect factor based on the body fat rate of the dog when it is entered thereto, and calculates the metabolism of the dog by taking into account of said thermal insulation effect factor. Accordingly, the metabolism can be calculated with higher precision by taking into account of effect on body temperature of adiabatic nature due to body fat.

The metabolism calculation unit calculates at least one of the basal metabolism and the metabolism in rest condition. Accordingly, either of data can be used as necessary.

The metabolism calculation unit includes an action data input unit for entering action data of the dog and a total energy consumption calculation unit for calculating total energy consumption of the dog based on the metabolism and the action data. Accordingly, total energy consumption for each of dogs can be calculated.

The action data is action indices each indicating ordinary action of the dog with a plurality of steps. Accordingly, total energy consumption can easily be calculated simply by selecting the action of the dog.

The action data is exercise data measured by an exercise monitoring device such as a pedometer, an accelerator, etc. Accordingly, energy consumption due to an exercise can precisely be calculated.

The total energy consumption calculation unit includes an adiposity related data input unit for entering adiposity related data of the dog, a target weight reduction setting unit for setting target weight reduction, and a proper value calculation unit for calculating at least one of proper intake energy or proper consumption energy relative to said target weight reduction, based on said total energy consumption, said adiposity related data and said target weight reduction. Accordingly, health care of the dog with proper amount of food or proper exercise load can be provided.

The adiposity related data is weight value and body fat data of the dog. Accordingly, the degree of adiposity for the dog can clearly be indicated with the numerical value, which facilitates setting of target weight reduction.

The body fat data is body fat mass or body fat rate calculated using at least one of impedance value of the dog, body condition score and morphologic measurement data. Accordingly, either of them can easily be calculated.

The target weight reduction is a general standard value for adiposity that is automatically set as the target. Accordingly, weight reduction giving lesser burden to the dog can be carried out.

The target weight reduction is set by a measurement person who manually enters numerical value. Accordingly, the person can freely set the target value for each of dogs.

The total energy consumption calculation unit includes an ambient temperature input unit for entering ambient temperature, and calculates total energy consumption by taking into account of the ambient temperature. Accordingly, any variation in energy consumption depending on cold and warm can be corrected.

The ambient temperature is set in advance for every season or every month so that it is automatically entered. Accordingly, the ambient temperature can easily be corrected.

The invention claimed is:

1. An animal health care system, comprising:
a weight input unit;
an impedance measurement unit;
an inter-leg distance input unit; and
a health assessment data calculation unit, wherein
said weight input unit is configured to enter a weight value of an animal,
said impedance measurement unit includes a plurality of impedance measurement electrodes for respectively contacting a root of each leg of the animal, and said impedance measuring unit measures impedance between front and rear legs of the animal,
said inter-leg distance input unit is configured to enter the distance between the roots of front and rear legs of the animal, and
said health assessment data calculation unit is configured to calculate health assessment data based on the weight value of the animal, the impedance between front and rear legs of the animal, and the distance between the roots of front and rear legs of the animal,
wherein said weight input includes a restriction unit configured to place and keep at least one of the chest, abdomen and roots of the legs of the animal in position, and to measure and enter the weight of the animal, and
wherein said restriction unit includes a lift unit for changing a height of the restriction unit for restricting the animal such that the legs of the animal are not in contact with any part of the health care system other than the restriction unit.

2. An animal health care system according to claim 1, wherein said impedance measurement electrode comprises one of a flexible electrically conductive material including an electrically conductive resin, a flexible electrically conductive material including an electrically conductive rubber, an electrically conductive member having a spherical portion, and an electrically conductive member having a spring-like portion for contacting the skin of the animal.

3. An animal health care system according to claim 1 in which said impedance measurement electrodes each have a plurality of projected portions formed on a surface thereof for making sure to contact the skin of the animal irrespective of presence of body hair.

4. An animal health care system according to claim 1 in which said impedance measurement electrode has a cushion material including either of sponge and cloth, provided on the surface thereof for providing water-keeping capability.

5. An animal health care system according to claim 1 in which said impedance measurement electrode includes a constant pressure unit for producing constant pressure to make contact with the animal at the level of not stimulating the animal.

6. An animal health care system according to claim 1 in which said health assessment data calculation unit calculates the health assessment data by taking into account at least one of morphologic measurement data including body length, body height, girth of trunk, girth of chest or girth of waist of the animal.

7. An animal health care system according to claim 1 in which said restriction unit comprises the inter-leg distance input unit, said restriction unit includes contact portions for respectively contacting the root of each leg of the animal, and said restriction unit is configured to automatically measure and enter the distance between the contact portions.

8. An animal health care system according to claim 1 in which said restriction unit comprises the impedance measuring unit, and includes contact portions for respectively contacting the root of each leg of the animal, each contact portion comprising of one of the impedance measurement electrodes.

9. An animal health care system according to claim 1 in which said restriction unit has a width or height for receiving the animal, which can be adjusted according to the size of the animal.

10. An animal health care system according to claim 1 in which said restriction unit includes a flexible net or meshed sheet configured to let at least four legs of the animal pass through, and frames configured to secure the net at any condition from a spread condition to a folded condition.

11. An animal health care system according to claim 10 in which said frames are secured to said lift unit, and said lift unit is configured to narrow the spacing between two said frames with an increasing height of the lift unit.

12. An animal health care system according to any one of claims 1–6, 7–8 and 9–11 in which said health assessment data calculated by the health assessment data calculation unit is body water mass of the animal.

13. An animal health care system according to any one of claims 1–6, 7–8 and 9–11 in which said health assessment data calculated by the health assessment data calculation unit is fat free mass of the animal.

14. An animal health care system according to any one of claims 1–6, 7–8 and 9–11 in which said health assessment data calculated by the health assessment data calculation unit is body fat mass of the animal.

15. An animal health care system according to any one of claims 1–6, 7–8 and 9–11 in which said health assessment data calculation unit includes a "BCS" (Body Condition Score) estimation unit for estimating "BCS" based on the health assessment data calculated.

16. An animal health care system according to any one of claims 1–6, 7–8 and 9–11 in which said health assessment data calculation unit includes an adiposity judgment unit for judging the degree of adiposity of the animal based on the health assessment data calculated.

17. An animal health care system, comprising:
a fat free data input unit;
a body temperature related data input unit;
a body temperature correction factor derivation unit; and
a metabolism calculation unit, wherein
said fat free data input unit enters fat free data of a dog,
said body temperature related data input unit enters body temperature related data of the dog,
said body temperature correction factor derivation unit derives a body temperature correction factor based on at least one of a kind of dog and a body build of the dog, and
said metabolism calculation unit calculates a metabolism of the dog based on said fat free data and said body temperature correction factor.

18. An animal health care system according to claim 17 in which said fat free data is fat free mass or amount of muscle.

19. An animal health care system according to claim 17 in which said fat free data is derived from weight value and body fat data.

20. An animal health care system according to claim 17 in which said body build of the dog is body mass index estimated from a weight value.

21. An animal health care system according to claim 17 in which said metabolism calculation unit includes a body hair data input unit for entering body hair data of the dog, and calculates the metabolism of the dog by taking into account of the body hair data entered thereby.

22. An animal health care system according to claim 17 in which said metabolism calculation unit includes an age input unit for entering the age of the dog, and calculates the metabolism of the dog by taking into account of the age.

23. An animal health care system according to claim 17 in which said metabolism calculation unit includes a thermal insulation effect factor derivation unit for deriving thermal insulation effect factor based on the body fat rate of the dog when it is entered thereto, and calculates the metabolism of the dog by taking into account of said thermal insulation effect factor.

24. An animal health care system according to claim 17 in which said metabolism calculation unit calculates at least one of a basal metabolism and a metabolism in rest condition.

25. An animal health care system according to claim 17 in which said metabolism calculation unit includes an action data input unit for entering action data of the dog and a total energy consumption calculation unit for calculating total energy consumption of the dog based on the metabolism and the action data.

26. An animal health care system according to claim 25 in which said action data is action indices each indicating ordinary action of the dog with a plurality of steps.

27. An animal health care system according to claim 25 in which said action data is exercise data measured by an exercise monitoring device including at least one of a pedometer and an accelerator.

28. An animal health care system according to claim 25 in which said total energy consumption calculation unit includes an adiposity related data input unit for entering adiposity related data of the dog, a target weight reduction setting unit for setting target weight reduction, and a proper value calculation unit for calculating at least one of proper intake energy or proper consumption energy relative to said target weight reduction, based on said total energy consumption, said adiposity related data and said target weight reduction.

29. An animal health care system according to claim 28 in which said adiposity related data is weight value and body fat data of the dog.

30. An animal health care system according to claim 19 or 29 in which said body fat data is body fat mass or body fat rate calculated using at least one of impedance value of the dog, body condition score or morphologic measurement data.

31. An animal health care system according to claim 28 in which said target weight reduction is a general standard value for adiposity that is automatically set as the target.

32. An animal health care system according to claim 28 in which said target weight reduction is set by a measurement person who manually enters the numerical value.

33. An animal health care system according to claim 25 in which said total energy consumption calculation unit includes an ambient temperature input unit for entering ambient temperature, and calculates total energy consumption by taking into account of the ambient temperature.

34. An animal health care system according to claim 33 in which said ambient temperature is set in advance for every season or every month so that it is automatically entered.

* * * * *